US010010306B2

(12) United States Patent
Kawashima

(10) Patent No.: US 10,010,306 B2
(45) Date of Patent: Jul. 3, 2018

(54) ULTRASOUND DIAGNOSIS APPARATUS, METHOD FOR OPERATING ULTRASOUND DIAGNOSIS APPARATUS, AND COMPUTER-READABLE RECORDING MEDIUM

(71) Applicant: OLYMPUS CORPORATION, Hachioji (JP)

(72) Inventor: Tomonao Kawashima, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/223,167

(22) Filed: Jul. 29, 2016

(65) Prior Publication Data

US 2016/0331352 A1    Nov. 17, 2016

Related U.S. Application Data

(63) Continuation of application No. PCT/JP2015/078247, filed on Oct. 5, 2015.

(30) Foreign Application Priority Data

Dec. 22, 2014    (JP) ................................ 2014-259470

(51) Int. Cl.
*A61B 8/00*    (2006.01)
*A61B 8/08*    (2006.01)
(Continued)

(52) U.S. Cl.
CPC .............. *A61B 8/5269* (2013.01); *A61B 8/12* (2013.01); *A61B 8/461* (2013.01); *A61B 8/5207* (2013.01);
(Continued)

(58) Field of Classification Search
CPC .......................... G01S 7/52036; A61B 8/0875
See application file for complete search history.

(56) References Cited

U.S. PATENT DOCUMENTS

2010/0087736 A1    4/2010  Katsuyama
2013/0035594 A1    2/2013  Eda
(Continued)

FOREIGN PATENT DOCUMENTS

CN    104207804 A    12/2014
JP    2010-82230 A    4/2010
(Continued)

OTHER PUBLICATIONS

International Search Report dated Dec. 15, 2015 issued in Application No. PCT/JP2015/078247.

*Primary Examiner* — Hien Nguyen
(74) *Attorney, Agent, or Firm* — Scully, Scott, Murphy & Presser, P.C.

(57) ABSTRACT

An ultrasound diagnosis apparatus is configured to generate an ultrasound image based on an ultrasound signal obtained by an ultrasound probe having an ultrasound transducer that transmits ultrasound to a subject and receives the ultrasound reflected from the subject. The apparatus includes: an analysis unit that analyzes a frequency of the ultrasound signal to calculate a frequency spectrum of the ultrasound signal for each reception depth; a calculation unit that calculates, in a predetermined order, a distance change rate and a frequency change rate in the frequency spectrum or in a function defined by using the frequency spectrum, to calculate a second-order change rate of the frequency spectrum or of the function; and an estimation unit that estimates an attenuation rate of the ultrasound signal, per unit distance and per unit frequency, in a predetermined region within a scanning region of the ultrasound transducer using the second-order change rate.

16 Claims, 15 Drawing Sheets

(51) Int. Cl.
  *A61B 8/12*   (2006.01)
  *G01S 15/89*  (2006.01)
  *G01S 7/52*   (2006.01)
  *A61B 8/14*   (2006.01)

(52) U.S. Cl.
  CPC ...... *G01S 7/52036* (2013.01); *G01S 7/52074* (2013.01); *G01S 15/8977* (2013.01); *A61B 8/14* (2013.01)

(56) References Cited

U.S. PATENT DOCUMENTS

| | | |
|---|---|---|
| 2014/0114189 A1 | 4/2014 | Kanayama et al. |
| 2015/0178919 A1 | 6/2015 | Noguchi |

FOREIGN PATENT DOCUMENTS

| | | |
|---|---|---|
| JP | 2013-5876 A | 1/2013 |
| JP | 2013-166059 A | 8/2013 |
| JP | 5659324 B1 | 1/2015 |
| WO | 2014/192954 A1 | 12/2014 |

ULTRASOUND DIAGNOSIS APPARATUS, METHOD FOR OPERATING ULTRASOUND DIAGNOSIS APPARATUS, AND COMPUTER-READABLE RECORDING MEDIUM

CROSS REFERENCES TO RELATED APPLICATIONS

This application is a continuation of PCT international application Ser. No. PCT/JP2015/078247, filed on Oct. 5, 2015 which designates the United States, incorporated herein by reference, and which claims the benefit of priority from Japanese Patent Application No. 2014-259470, filed on Dec. 22, 2014, incorporated herein by reference.

BACKGROUND

1. Technical Field

The disclosure relates to an ultrasound diagnosis apparatus configured to generate an ultrasound image based on an ultrasound signal obtained by an ultrasound probe that transmits ultrasound to a subject and receives the ultrasound reflected from the subject. The disclosure also relates to a method for operating the ultrasound diagnosis apparatus, and a computer-readable recording medium.

2. Related Art

In an ultrasound diagnosis apparatus that generates an ultrasound image based on an ultrasound signal obtained by an ultrasound probe that transmits ultrasound to a subject and receives the ultrasound reflected from the subject, there is a known technique of calculating an attenuation rate of the ultrasound inside the subject (for example, refer to JP 2010-82230 A). In this technique, a Gaussian pulse is transmitted from an ultrasound probe to a subject, and along with this, performs quadrature detection onto a reception signal output from the ultrasound probe to obtain a phase $\phi(t)$ indicating a phase of an ultrasound echo, so as to obtain second-order differential value $d^2\phi/dt^2$ for time t from which a speckle component has been removed. In JP 2010-82230 A, an attenuation rate $\alpha$ is calculated using a relational equation $$d^2\phi/dt^2 = 2\pi\alpha \times (\Delta w)^2 \times v \qquad (1)$$

satisfied by attenuation per unit distance (attenuation rate in JP 2010-82230 A) $\alpha$, the second-order differential value $d^2\phi/dt^2$, sound velocity v, and known bandwidth $\Delta w$ ($\pi$ represents the ratio of the circumference of a circle to its diameter). JP 2010-82230 A merely describes acquisition of the sound velocity v using another technique and does not disclose details of the technique.

There is a known ultrasound diagnosis apparatus that differentiates a noise region as a low S/N region and displays this information on the low S/N region with an attenuation image as an image based on the attenuation rate (for example, refer to JP 2013-5876 A). This technique stops transmission of ultrasound under a condition equal to a case of transmitting and receiving an ultrasound signal having a center frequency of 4 MHz and generates a noise image based on a noise signal received from individual positions of the subject. During the examination, brightness of the noise image is compared with brightness of a B-mode image with 4 MHz, a pixel having the same brightness is extracted as a low S/N region, and then, information on the pixel on this low S/N region and the attenuation image generated separately are displayed on a monitor.

SUMMARY

In some embodiments, an ultrasound diagnosis apparatus is configured to generate an ultrasound image based on an ultrasound signal obtained by an ultrasound probe having an ultrasound transducer that transmits ultrasound to a subject and receives the ultrasound reflected from the subject. The ultrasound diagnosis apparatus includes: a frequency analysis unit configured to analyze a frequency of the ultrasound signal to calculate a frequency spectrum of the ultrasound signal for each reception depth; a change rate calculation unit configured to calculate, in a predetermined order, a distance change rate and a frequency change rate in the frequency spectrum calculated by the frequency analysis unit or in a function defined by using the frequency spectrum, thereby to calculate a second-order change rate of the frequency spectrum or of the function; and an attenuation rate estimation unit configured to estimate an attenuation rate of the ultrasound signal, per unit distance and per unit frequency, in a predetermined region within a scanning region of the ultrasound transducer using the second-order change rate calculated by the change rate calculation unit.

In some embodiments, a method for operating an ultrasound diagnosis apparatus is provided. The ultrasound diagnosis apparatus is configured to generate an ultrasound image based on an ultrasound signal obtained by an ultrasound probe having an ultrasound transducer that transmits ultrasound to a subject and receives the ultrasound reflected from the subject. The method includes: by a frequency analysis unit, analyzing a frequency of the ultrasound signal to calculate a frequency spectrum of the ultrasound signal for each reception depth; by a change rate calculation unit, calculating, in a predetermined order, a distance change rate and a frequency change rate in the frequency spectrum or in a function defined by using the frequency spectrum, thereby calculating a second-order change rate of the frequency spectrum or of the function; and by an attenuation rate estimation unit, estimating an attenuation rate of the ultrasound signal, per unit distance and per unit frequency, in a predetermined region within a scanning region of the ultrasound transducer using the second-order change rate.

In some embodiments, a non-transitory computer-readable recording medium with an executable program stored thereon is provided. The program causes an ultrasound diagnosis apparatus that is configured to generate an ultrasound image based on an ultrasound signal obtained by an ultrasound probe having an ultrasound transducer that transmits ultrasound to a subject and receives the ultrasound reflected from the subject, to execute: by a frequency analysis unit, analyzing a frequency of the ultrasound signal to calculate a frequency spectrum of the ultrasound signal for each reception depth; by a change rate calculation unit, calculating, in a predetermined order, a distance change rate and a frequency change rate in the frequency spectrum or in a function defined by using the frequency spectrum, thereby calculating a second-order change rate of the frequency spectrum or of the function; and by an attenuation rate estimation unit, estimating an attenuation rate of the ultrasound signal, per unit distance and per unit frequency, in a predetermined region within a scanning region of the ultrasound transducer using the second-order change rate.

The above and other features, advantages and technical and industrial significance of this invention will be better understood by reading the following detailed description of presently preferred embodiments of the invention, when considered in connection with the accompanying drawings.

DETAILED DESCRIPTION

Hereinafter, modes for carrying out the present invention (hereinafter, referred to as embodiment(s)) will be described with reference to the attached drawings.

First Embodiment

Figure 1:
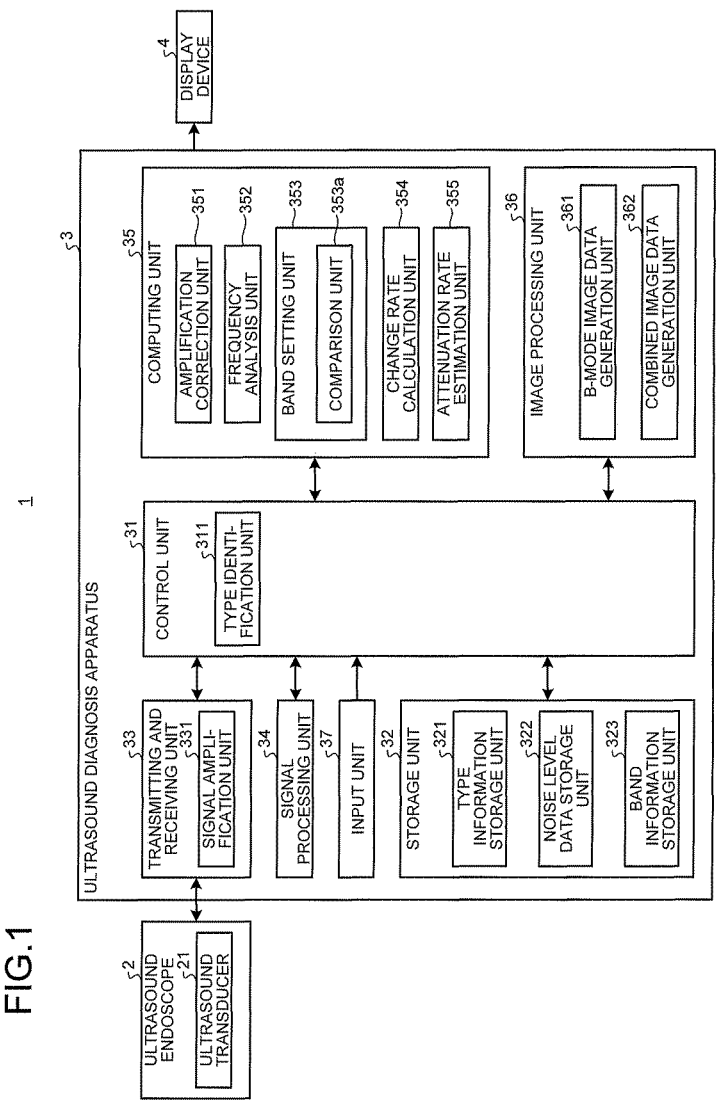
FIG. 1 is a block diagram illustrating a functional configuration of an ultrasound diagnosis system equipped with an ultrasound diagnosis apparatus according to a first embodiment of the present invention.

FIG. 1 is a block diagram illustrating a functional configuration of an ultrasound diagnosis system equipped with an ultrasound diagnosis apparatus according to a first embodiment of the present invention. An ultrasound diagnosis system 1 illustrated in FIG. 1 includes an ultrasound endoscope 2, an ultrasound diagnosis apparatus 3, and a display device 4. The ultrasound endoscope 2 transmits ultrasound to a subject and receives the ultrasound reflected from the subject. The ultrasound diagnosis apparatus 3 generates an ultrasound image based on an ultrasound signal obtained by the ultrasound endoscope 2. The display device 4 displays the ultrasound image generated by the ultrasound diagnosis apparatus 3.

The ultrasound endoscope 2 includes, on its distal end, an ultrasound transducer 21. The ultrasound transducer 21 converts an electrical pulse signal received from the ultrasound diagnosis apparatus 3 into an ultrasound pulse (acoustic pulse) and emits it to the subject. The ultrasound transducer 21 also converts an ultrasound echo reflected from the subject into an electrical echo signal expressed by a voltage change and outputs the signal. The ultrasound endoscope 2 may cause the ultrasound transducer 21 to perform mechanical scan, or may provide, as the ultrasound transducer 21, a plurality of elements in an array, and may cause the ultrasound transducer to perform electronic scan by electronically switching elements related to transmission/reception or imposing delay onto transmission/reception of each of elements.

The ultrasound endoscope 2 typically includes imaging optics and imaging elements. The ultrasound endoscope 2 can be inserted into gastrointestinal tracts (esophagus, stomach, duodenum, and large intestine) or respiratory organs (trachea, bronchus) of the subject and can image gastrointestinal tract, respiratory organs, and their surrounding organs (pancreas, gall bladder, bile duct, biliary tract, lymph nodes, mediastinal organs, blood vessels, or the like). The ultrasound endoscope 2 includes a light guide that guides illumination light emitted to the subject at the time of imaging. The light guide is configured such that a distal end portion thereof reaches a distal end of an insertion portion of the ultrasound endoscope 2 into the subject, while a proximal end thereof is connected to a light source device that generates illumination light.

The ultrasound diagnosis apparatus 3 includes a control unit 31, a storage unit 32, a transmitting and receiving unit 33, a signal processing unit 34, a computing unit 35, an image processing unit 36, and an input unit 37. The control unit 31 controls the overall ultrasound diagnosis system 1. The storage unit 32 stores various types of information needed for operation of the ultrasound diagnosis apparatus 3. The transmitting and receiving unit 33 is electrically connected with the ultrasound endoscope 2, transmits a transmission signal (pulse signal) formed with a high-voltage pulse to the ultrasound transducer 21 based on a predetermined waveform and transmission timing, and together with this, receives an echo signal, namely, an electrical reception signal, from the ultrasound transducer 21, generates digital radio frequency (RF) signal data (hereinafter, referred to as RF data), and outputs the generated data. The signal processing unit 34 generates digital reception data for B-mode based on the RF data received from the transmitting and receiving unit 33. The computing unit 35 performs predetermined calculation on the RF data received from the transmitting and receiving unit 33. The image processing unit 36 generates various image data. The input unit 37 includes a user interface such as a keyboard, a mouse, and a touch panel, and receives input of various types of information.

The control unit 31 includes a type identification unit 311 configured to determine the type of the ultrasound endoscope 2 connected to the ultrasound diagnosis apparatus 3. The type identification unit 311 identifies the type of the ultrasound transducer 21 by obtaining ID stored in a memory inside the ultrasound endoscope 2 connected to the ultrasound diagnosis apparatus 3. Information related to the type of the ultrasound transducer 21 identified by the type identification unit 311 is stored in a type information storage unit 321 of the storage unit 32, described below. The type identification unit 311 may be configured to identify the type of the ultrasound transducer 21 based on the type name of the ultrasound endoscope 2 on which the input unit 37 has received input.

The control unit 31 includes a central processing unit (CPU) having calculation and control functions, various calculation circuits, or the like. The control unit 31 integrally controls the ultrasound diagnosis apparatus 3 by reading information stored in the storage unit 32 and various programs including an operation program of the ultrasound diagnosis apparatus 3, from the storage unit 32, and executing various types of calculation processing related to an operation method of the ultrasound diagnosis apparatus 3.

The storage unit 32 includes a type information storage unit 321, a noise level data storage unit 322, and a band information storage unit 323. The type information storage unit 321 stores type information of the ultrasound transducer 21, identified by the type identification unit 311. The noise level data storage unit 322 stores noise level data for individual types of the ultrasound transducer 21 connectable to the ultrasound diagnosis apparatus 3. The band information storage unit 323 stores frequency band information as a target of regression analysis performed by the computing unit 35, for individual types of the ultrasound transducer 21 connectable to the ultrasound diagnosis apparatus 3.

Figure 2:
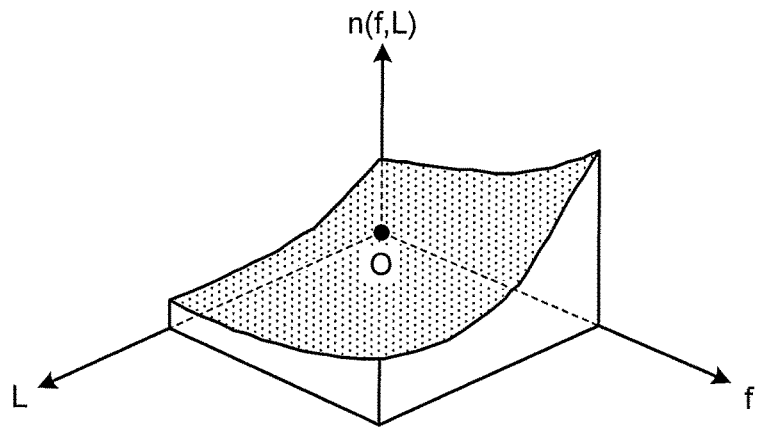
FIG. 2 is a diagram schematically illustrating noise level data stored in a noise level data storage unit included in the ultrasound diagnosis apparatus according to the first embodiment of the present invention.

FIG. 2 is a diagram schematically illustrating noise level data stored in the noise level data storage unit 322. In FIG. 2, a curved surface indicated by dots provides noise level data n(f, L). The noise level data n(f, L) is a function having a frequency f of the ultrasound echo, and a reciprocating distance L (a distance being twice the reception depth) between a surface of the ultrasound transducer 21 and the subject (reflector) as discrete variables. The noise level data n(f, L) are discrete digital data expressed, for example, in decibel value (dB) obtained by dividing a voltage V corresponding to the noise by a reference voltage $V_c$ and then taking a common logarithm of this amount. Hereinafter, the reciprocating distance L between the surface of the ultrasound transducer 21 and the subject will be referred to simply as a distance L, in some cases.

The noise level data storage unit 322 stores noise level data for individual types of the ultrasound transducer 21 connectable to the ultrasound diagnosis apparatus 3. The noise level data are, for example, preliminary measured and stored for individual types of the ultrasound transducer 21 as factory presets. It is also allowable to store, as noise level data, echo signals received when transmission by the transmitting and receiving unit 33 is stopped. In this case, it is possible to obtain more specific noise level data that account for not only the type of the ultrasound transducer 21 but also individual variation in the ultrasound transducer 21 of a same type and the noise level difference within a same subject due to a change over time.

The band information storage unit 323 stores, as band information as a regression analysis target by the computing unit 35, information related to a minimum value fmin and a maximum value fmax of the frequency band for individual types of the ultrasound transducer 21 connectable to the ultrasound diagnosis apparatus 3. Similarly to the noise level data, the band information is preliminary measured and stored for individual types of the ultrasound transducer 21, as factory presets.

In addition to the above, the storage unit 32 also stores information needed for various types of processing performed by the transmitting and receiving unit 33, the signal processing unit 34, and the computing unit 35.

The storage unit 32 stores various programs including an operation program for executing an operation method of the ultrasound diagnosis apparatus 3. The various programs can be recorded in a computer-readable recording medium such as a hard disk, flash memory, CD-ROM, DVD-ROM, flexible disk, or the like, and can be distributed broadly. It is also possible to obtain the above-described various programs by downloading them via a communication network. Herein, the communication network refers to one implemented by, for example, a known public network, a local area network (LAN), a wide area network (WAN), regardless of wired or wireless.

The storage unit 32 with the above-described configuration is implemented using a read only memory (ROM) in which various programs are pre-installed, a random access memory (RAM) storing calculation parameters and data for individual processing, a hard disk drive (HDD), or the like.

Figure 3:
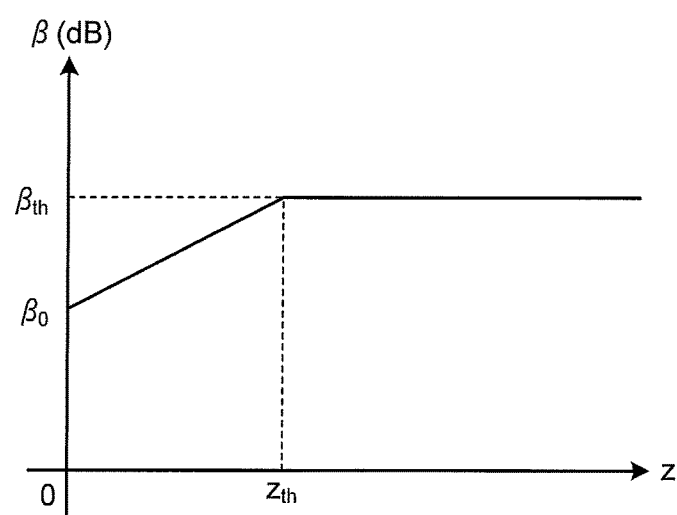
FIG. 3 is a diagram illustrating a relationship between a reception depth and an amplification factor in amplification processing performed by a signal amplification unit included in the ultrasound diagnosis apparatus according to the first embodiment of the present invention.

The transmitting and receiving unit 33 includes a signal amplification unit 331 that amplifies an echo signal. The signal amplification unit 331 performs sensitivity time control (STC) correction that amplifies an echo signal having a larger reception depth by using a higher amplification factor. FIG. 3 is a diagram illustrating a relationship between a reception depth and an amplification factor in amplification processing performed by the signal amplification unit 331. A reception depth z illustrated in FIG. 3 is an amount calculated based on elapsed time from a point of starting reception of ultrasound. As illustrated in FIG. 3, in a case where the reception depth z is smaller than a threshold $z_{th}$, an amplification factor R (dB) increases linearly along with an increase in the reception depth z from $\beta_0$ to $\beta_{th}$ ($>\beta_0$). In a case where the reception depth z is equal to or higher than the threshold $z_{th}$, the amplification factor $\beta$ (dB) takes a constant value $\beta_{th}$. The value of the threshold $z_{th}$ is a value at which an ultrasound signal received from the subject is nearly completely attenuated and noise is dominant. More typically, in a case where the reception depth z is smaller than the threshold $z_{th}$, the amplification factor $\beta$ a may preferably increase monotonically along with an increase in the reception depth z. The relationship illustrated in FIG. 3 is pre-stored in the storage unit 32.

The transmitting and receiving unit 33 performs processing such as filtering on the echo signal amplified by the signal amplification unit 331, thereafter, generates RF data of time domain by performing A/D conversion on the signal, and outputs the RF data to the signal processing unit 34 and the computing unit 35. In a case where the ultrasound endoscope 2 is configured to perform scanning electronically with the ultrasound transducer 21 having a plurality of elements arranged in array, the transmitting and receiving unit 33 includes a beam-combining multi-channel circuit corresponding to the plurality of elements.

The frequency band of the pulse signal transmitted by the transmitting and receiving unit 33 is preferably a broadband substantially covering a linear response frequency band for electroacoustic conversion from pulse signals to ultrasound pulses on the ultrasound transducer 21. With this configuration, it is possible to perform accurate approximation in approximation processing of a frequency spectrum described below.

The transmitting and receiving unit 33 has a function of transmitting various control signals output by the control unit 31, to the ultrasound endoscope 2, and together with this, has a function of receiving various types of information including identification ID from the ultrasound endoscope 2 and transmitting the information to the control unit 31.

Figure 4:
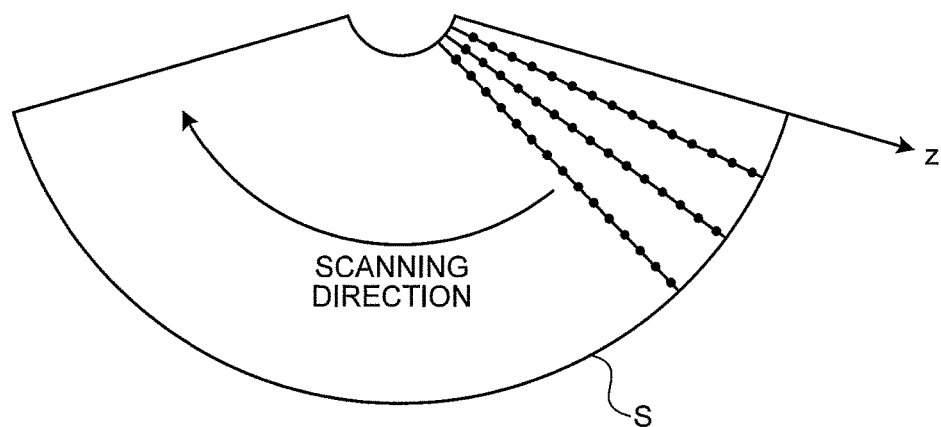
FIG. 4 is a diagram schematically illustrating a scanning region of an ultrasound transducer, and reception data for B-mode.

The signal processing unit 34 performs known processing such as a band-pass filter, envelope detection, logarithmic transformation, on the RF data, and generates digital reception data for B-mode. In logarithmic transformation, a value is represented in decibel value by dividing RF data by the reference voltage $V_c$ and then taking a common logarithm of this amount. In the reception data for B-mode, amplitude or intensity of the reception signal indicating intensity of ultrasound pulse reflection is arranged along the transmission-reception direction (depth direction). FIG. 4 is a diagram schematically illustrating a scanning region of the ultrasound transducer 21 (hereinafter, also referred to simply as a scanning region) and reception data for B-mode. A scanning region S illustrated in FIG. 4 is fan-shaped. This corresponds to a case where the ultrasound transducer 21 is a convex transducer. In FIG. 4, the reception depth of the reception data for B-mode is illustrated as z. In a case where the ultrasound pulse emitted from the surface of the ultrasound transducer 21 is reflected from a reflector that is in the reception depth z and returned to the ultrasound transducer 21 as an ultrasound echo, there is a relationship of z=L/2 as described above between the reciprocating distance L and the reception depth z. The signal processing unit 34 outputs generated reception data for B-mode to a B-mode image data generation unit 361 of the image processing unit 36. The signal processing unit 34 is realized by a central processing unit (CPU), circuits for various types of calculation, or the like.

The computing unit 35 includes an amplification correction unit 351, a frequency analysis unit 352, a band setting unit 353, a change rate calculation unit 354, and an attenuation rate estimation unit 355. The amplification correction unit 351 performs amplification correction on the RF data output by the transmitting and receiving unit 33 such that an amplification factor is constant regardless of the reception depth. The frequency analysis unit 352 calculates a frequency spectrum for each of the reception depths, by performing frequency analysis with fast Fourier transform (FFT) performed on the amplification-corrected RF data. The band setting unit 353 sets a frequency band as a calculation target by comparing noise level data with frequency spectrum data. The change rate calculation unit 354 calculates a second-order change rate by calculating, with a predetermined order, a distance change rate and a frequency change rate in a function defined by the frequency spectrum calculated by the frequency analysis unit 352. The attenuation rate estimation unit 355 estimates an attenuation rate per unit distance and per unit frequency, of the ultrasound pulse in a scanning region using the second-order change rate calculated by the change rate calculation unit 354. The computing unit 35 includes a CPU and circuits for various types of calculation. The computing unit 35 can be configured with a CPU, or the like, shared with the control unit 31 and the signal processing unit 34.

Figure 5:
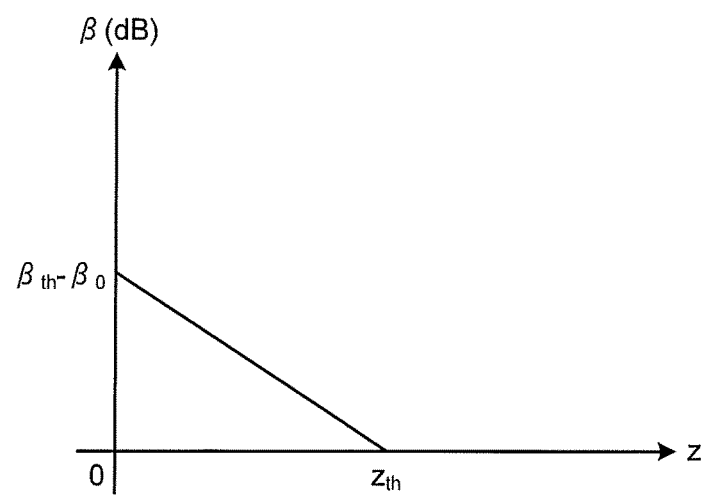
FIG. 5 is a diagram illustrating a relationship between a reception depth and an amplification factor in amplification correction processing performed by an amplification correction unit included in the ultrasound diagnosis apparatus according to the first embodiment of the present invention.

FIG. 5 is a diagram illustrating a relationship between a reception depth and an amplification factor in amplification correction processing performed by the amplification correction unit 351. As illustrated in FIG. 5, the amplification factor $\beta$ (dB) in amplification processing performed by the amplification correction unit 351 takes a maximum value $\beta_{th}-\beta_0$ when the reception depth z is zero, decreases linearly with the change in the reception depth z from zero until reaching the threshold $z_{th}$, and takes zero when the reception depth z is equal to or higher than the threshold $z_{th}$. The relationship illustrated in FIG. 5 is pre-stored in the storage unit 32. By amplification correction performed by the amplification correction unit 351 on the RF data based on the relationship illustrated in FIG. 5, it is possible to offset the effect of STC correction on the signal amplification unit 331 and to output a signal with a constant amplification factor $\beta_{th}$. The relationship between the reception depth z and the amplification factor $\beta$ in the amplification correction processing performed by the amplification correction unit 351 understandably differs depending upon the relationship between the reception depth and the amplification factor in the amplification correction processing performed by the signal amplification unit 331.

A reason for performing such amplification correction will be described. The STC correction is correction processing to exclude the effect of attenuation from amplitude of an analog signal waveform, by amplifying the amplitude of the analog signal waveform uniformly across an overall frequency band, with an amplification factor monotonically increasing with respect to the increase in the reception depth. Accordingly, in the case of generating a B-mode image in which amplitude of an echo signal is converted into brightness and displayed and in the case of scanning a uniform tissue, performing STC correction produces a constant brightness value regardless of depth. That is, it is possible to exclude the effect of attenuation from the brightness value of the B-mode image. Meanwhile, by utilizing a result of calculation and analysis of the frequency spectrum of the ultrasound, as in the first embodiment, it is difficult, even with the STC correction, to accurately exclude the effect of attenuation along with propagation of the ultrasound. The reason is that the attenuation differs depending on the frequency but the amplification factor of STC correction changes only for the distance, namely, takes a constant value for the frequency without any change.

In order to solve the above-described situation, namely the situation that, when utilizing a result of calculation and analysis of the frequency spectrum of the ultrasound, it is difficult, even with the STC correction, to accurately exclude the effect of attenuation along with the propagation of the ultrasound, one possibility may be that, while an STC-corrected reception signal is output in generating a B-mode image, a reception signal that has not undergone STC correction would be output, by performing new transmission besides the transmission to generate a B-mode image, in generating an image based on the frequency spectrum. In this case, however, the frame rate of image data generated based on the reception signal may be reduced.

In order to cope with this situation, the first embodiment performs correction of amplification factor, on the STC-corrected signal for B-mode image, by the amplification correction unit 351, in order to exclude the effect of STC correction, while maintaining frame rate of the image data to be generated.

The frequency analysis unit 352 generates sample data by sampling, in a predetermined time interval, RF data (line data) of individual sound rays amplification-corrected by the amplification correction unit 351. Subsequently, the frequency analysis unit 352 performs FFT processing on the sample data group, thereby calculating frequency spectrum on a plurality of locations (data positions) on the RF data.

Figure 6:
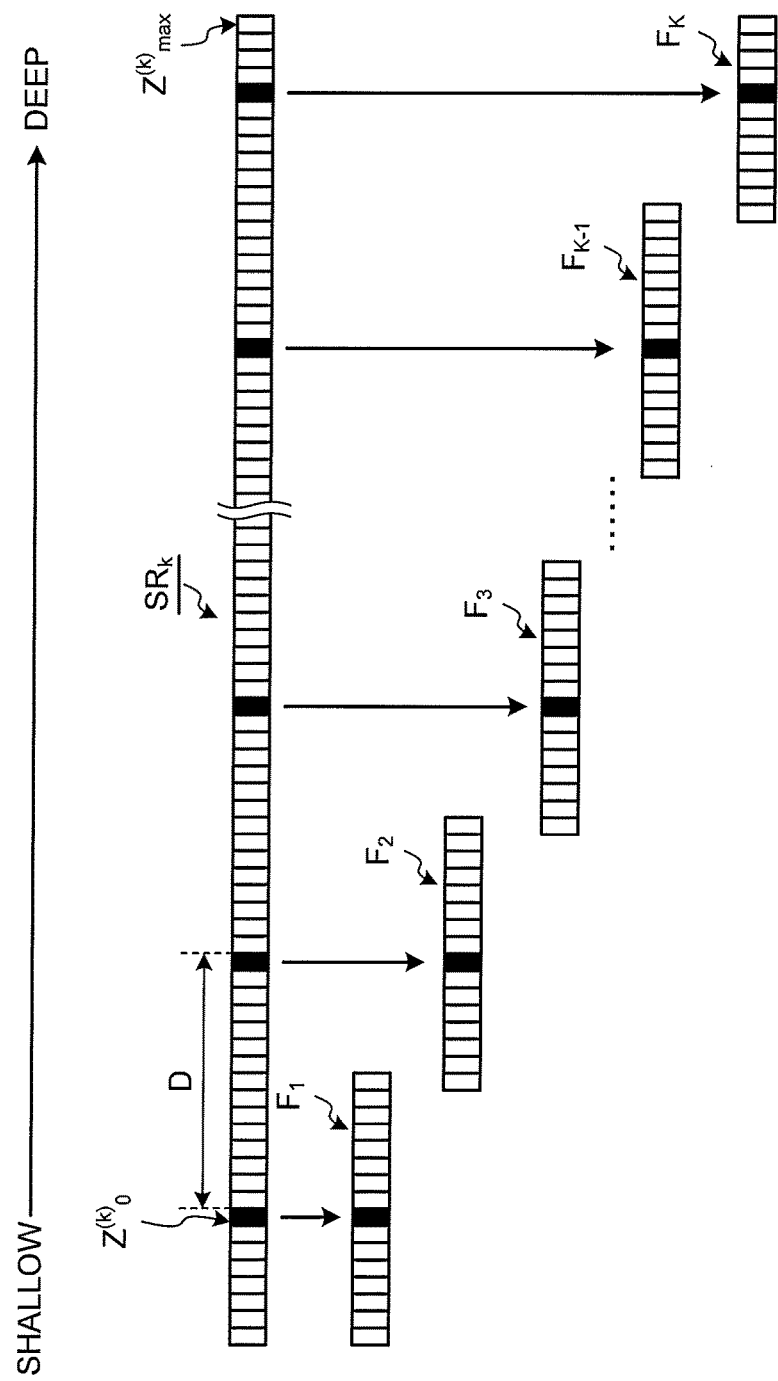
FIG. 6 is a diagram schematically illustrating data arrangement of a sound ray of an ultrasound signal.

FIG. 6 is a diagram schematically illustrating data arrangement of a sound ray of an ultrasound signal. In a sound ray $SR_k$ illustrated in FIG. 6, a white or black rectangle indicates data on one sample point. The data positioned at the more right direction of the sound ray $SR_k$ indicates sample data that is obtained from a deeper position in a case where measurement is performed from the ultrasound transducer 21 along the sound ray $SR_k$ (refer to arrows in FIG. 6). The sound ray $SR_k$ is discretized with a time interval corresponding to a sampling frequency (e.g. 50 MHz) in A/D conversion performed by the transmitting and receiving unit 33. FIG. 6 illustrates a case where an eighth data position of the sound ray $SR_k$ with the number k is set as an initial value $Z^{(k)}_0$ in the reception depth z direction. It is however allowable to set the position of the initial value arbitrarily. A result of calculation by the frequency analysis unit 352 is obtained as a complex number and stored in the storage unit 32.

A data group $F_j$ (j=1, 2, . . . , K) illustrated in FIG. 6 is a sample data group as a target of FFT processing. In general, in order to perform FFT processing, it is necessary that the sample data group has the number of data that is power of two. In this sense, while the sample data group $F_j$ (j=1, 2, . . . , K−1) has the number of data of 16 (=$2^4$), indicating it is a normal data group, the sample data group $F_K$ has the number of data of 12, indicating it is an abnormal data group. When FFT processing is performed on an abnormal data group, processing of generating a normal sample data group is performed by inserting zero data to cover the shortfall. This issue will be described in detail below, in the explanation of processing of the frequency analysis unit 352 (refer to FIG. 15).

The frequency analysis unit 352 generates a frequency component V(f, L) of a voltage amplitude by performing FFT processing on each of sample data groups removed from the RF data. The frequency component V(f, L) of the voltage amplitude is frequency density of the voltage. Furthermore, the frequency analysis unit 352 divides the frequency component V(f, L) of the voltage amplitude by the reference voltage $V_c$, and then, performs logarithmic transformation processing, namely, takes a common logarithm (log) and expresses it in a decibel unit. The frequency analysis unit 352 then multiplies the data with a suitable constant A, generates frequency spectrum data (hereinafter, also referred to as spectrum data) F(f, L) given by the next Formula (2), and outputs the generated data to the band setting unit 353.

$$F(f,L)=A\cdot\log\{V(f,L)/V_c\} \quad (2)$$

Herein, log represents common logarithm (hereinafter, the same will be applied).

Figure 7:
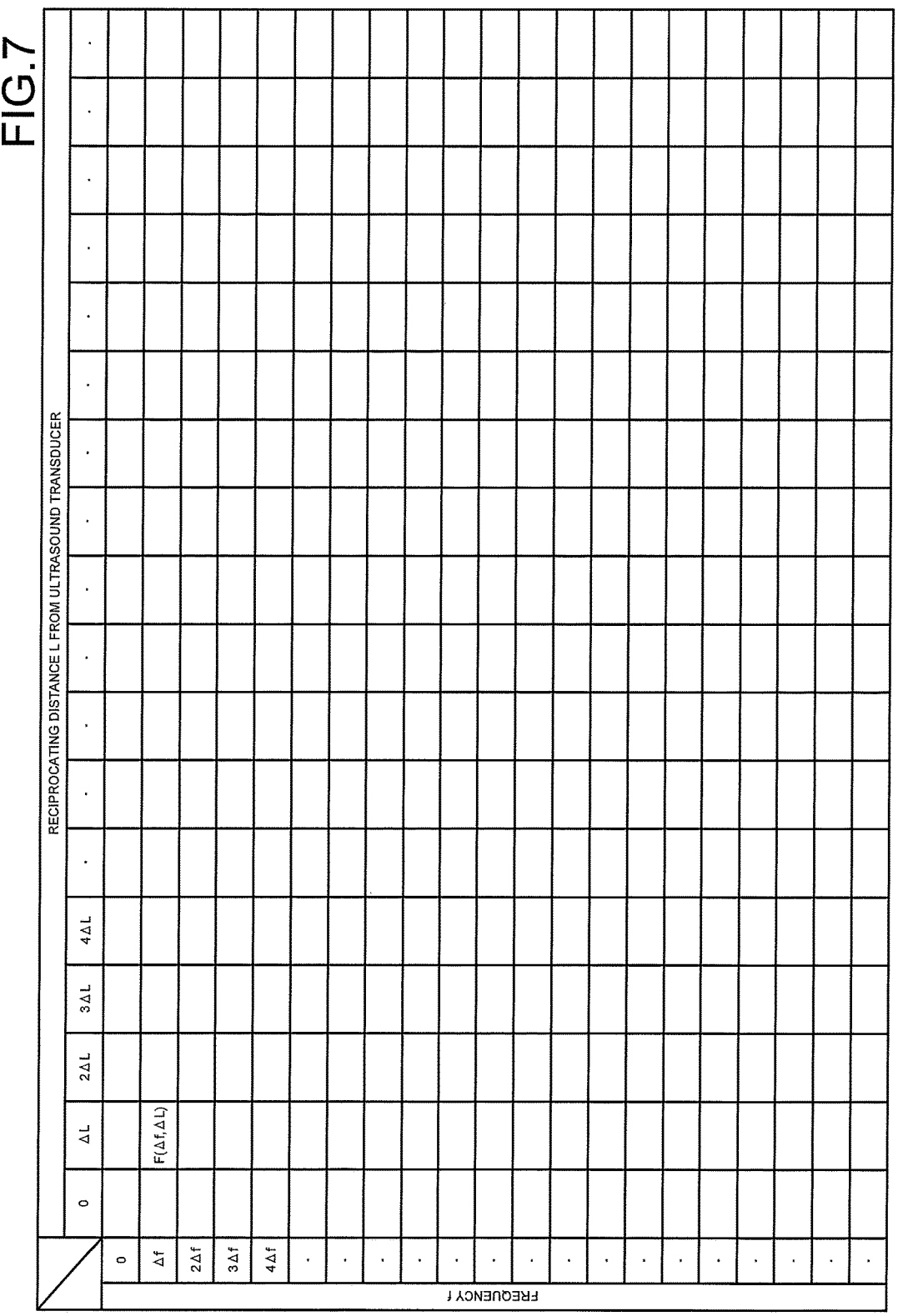
FIG. 7 is a diagram schematically illustrating a data string of a frequency spectrum.

The spectrum data F(f, L) are a component of a frequency f of a sample data group. FIG. 7 is a diagram schematically illustrating a data string of the spectrum data stored in the storage unit 32. In FIG. 7, the vertical direction represents the frequency f, and the horizontal direction represents a reciprocating distance L from the surface of the ultrasound transducer 21. The frequency f takes discrete values 0, Δf, 2Δf, . . . . For example, in a cell of column 0, spectrum data F(f, 0) obtained from Formula (2) based on the sample data group removed in the distance section 0≤L<ΔL are stored. In a cell of column ΔL, spectrum data F(f, ΔL) obtained from Formula (2) based on the sample data group removed at the section ΔL≤L<2ΔL of the distance L. In FIG. 7, only the spectrum data F(Δf, ΔL) are exemplified in cells of frequency Δf, and distance ΔL. In practice, however, it is obvious that spectrum data corresponding to the frequency and distance of each of the cells are stored in all the cells. An exemplary length ΔL (corresponding to step size D of sample data group in FIG. 6) of the section removed as the sample data group is about 1.0 cm. An exemplary amount of change Δf in the frequency is 0.5 MHz.

Figure 8:
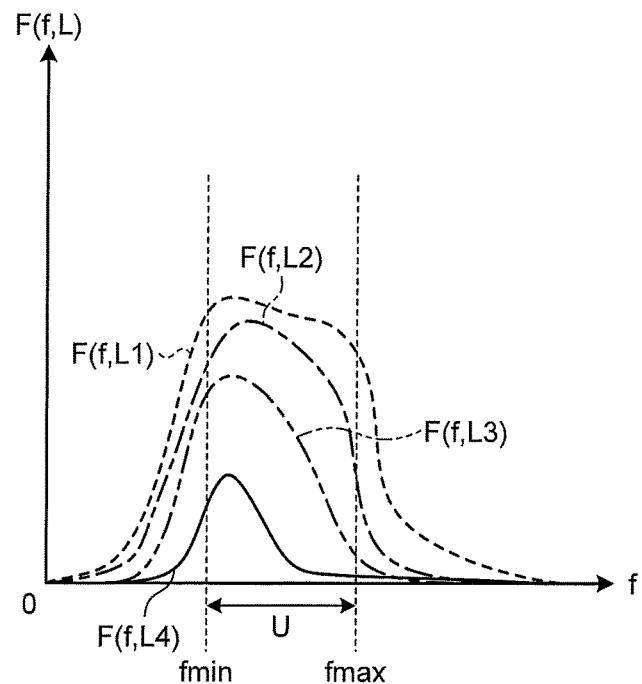
FIG. 8 is a diagram illustrating exemplary data of a frequency spectrum.

FIG. 8 is a diagram illustrating exemplary spectrum data. FIG. 8 illustrates a relationship between each of the spectrum data F(f, L1), F(f, L2), F(f, L3), and F(f, L4) on four mutually different distances, and the frequency f. The four distances L1, L2, L3, and L4 are constants satisfying 0<L1<L2<L3<L4. Although more spectrum data F(f, L) are calculated in practice as it is clear from FIG. 7, FIG. 8 exemplifies four representative spectrum data alone. As illustrated in FIG. 8, the spectrum data F(f, L) decreases as the distance L increases. The average frequency of the spectrum data F(f, L) shifts to the low-frequency side as the distance L increases. This is due to the effect of attenuation that depends on the frequency when the ultrasound propagates inside the subject.

In general, the spectrum data F(f, L) indicate different tendencies depending on attributes of the tissue that has undergone ultrasound scanning. This is because the spectrum data F(f, L) has a correlation with the size, number density, acoustic impedance, or the like, of a scatterer that scatters the ultrasound. Herein, exemplary "attributes" include malignant tumor tissues, benign tumor tissues, endocrine tumor tissues, mucinous tumor tissues, normal tissues, cysts, and vessels.

The band setting unit 353 includes a comparison unit 353a configured to compare the spectrum data F(f, L) with the noise level data n(f, L). To compare the above-described two types of data, the comparison unit 353a reads frequencies fmin and fmax at both ends of a frequency band U={f|fmin≤f≤fmax}, as a target of regression analysis described below, from the band information storage unit 323, according to the ultrasound transducer 21 connected to the ultrasound diagnosis apparatus 3. The frequency band U corresponds to a relatively flat section on a transmission waveform of the ultrasound on a surface (L=0) of the ultrasound transducer 21, and each of the minimum value fmin and the maximum value fmax varies according to the type of ultrasound transducer 21.

On the frequency band U read from the band information storage unit 323, the comparison unit 353a compares the spectrum data F(f, L) with the noise level data n(f, L), per frequency f, and per distance L. In comparison of four spectrum data F(f, Lp) (p=1, 2, 3, and 4) illustrated in FIG. 8 with corresponding noise level data n(f, Lp), assumption can be made, for example, such that, F(f, Lp)>n(f, Lp) is established at an arbitrary frequency f included in the frequency band U when p=1, 2, and 3, whereas the following two inequalities are established in the frequency band U when p=4.

$$F(f,L4)>n(f,L4)(fmin \le f<fmax')$$

$$F(f,L4) \le n(f,L4)(fmax' \le f \le fmax)$$

Figure 9:
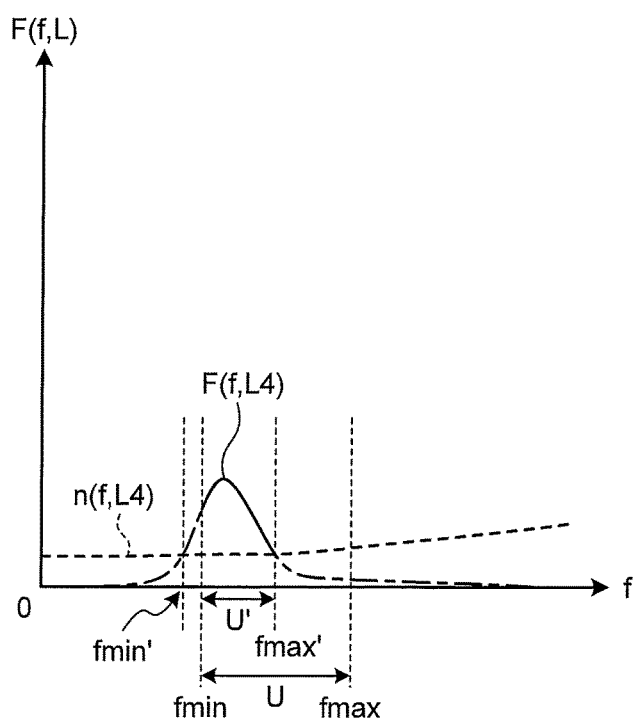
FIG. 9 is a diagram illustrating a relationship between data of a frequency spectrum and noise level data.

FIG. 9 is a diagram illustrating a relationship between the spectrum data F(f, L4) and the noise level data n(f, L4). In the case illustrated in FIG. 9, F(f, L4)≤n(f, L4) is established in two frequency bands f≤fmin', and f≥fmax', with the noise level data being dominant. Hereinafter, the frequency band in which the noise level data is dominant as in these two frequency bands will be referred to as a noise frequency band. As illustrated in FIG. 9, among the frequency fmin' and fmax', the one included in the frequency band U is fmax'.

The band setting unit 353 sets a frequency band as a regression analysis target based on a result of comparison by the comparison unit 353a. In the cases illustrated in FIGS. 8 and 9, the band setting unit 353 sets a regression analysis target for the distance Lp (p=1, 2, and 3) as an initial frequency band U, and together with this, sets a frequency band of the regression analysis target with the distance L=L4 as U'={f|fmin≤f<fmax'}, then, outputs the frequency band information to the attenuation rate estimation unit 355.

Figure 10:
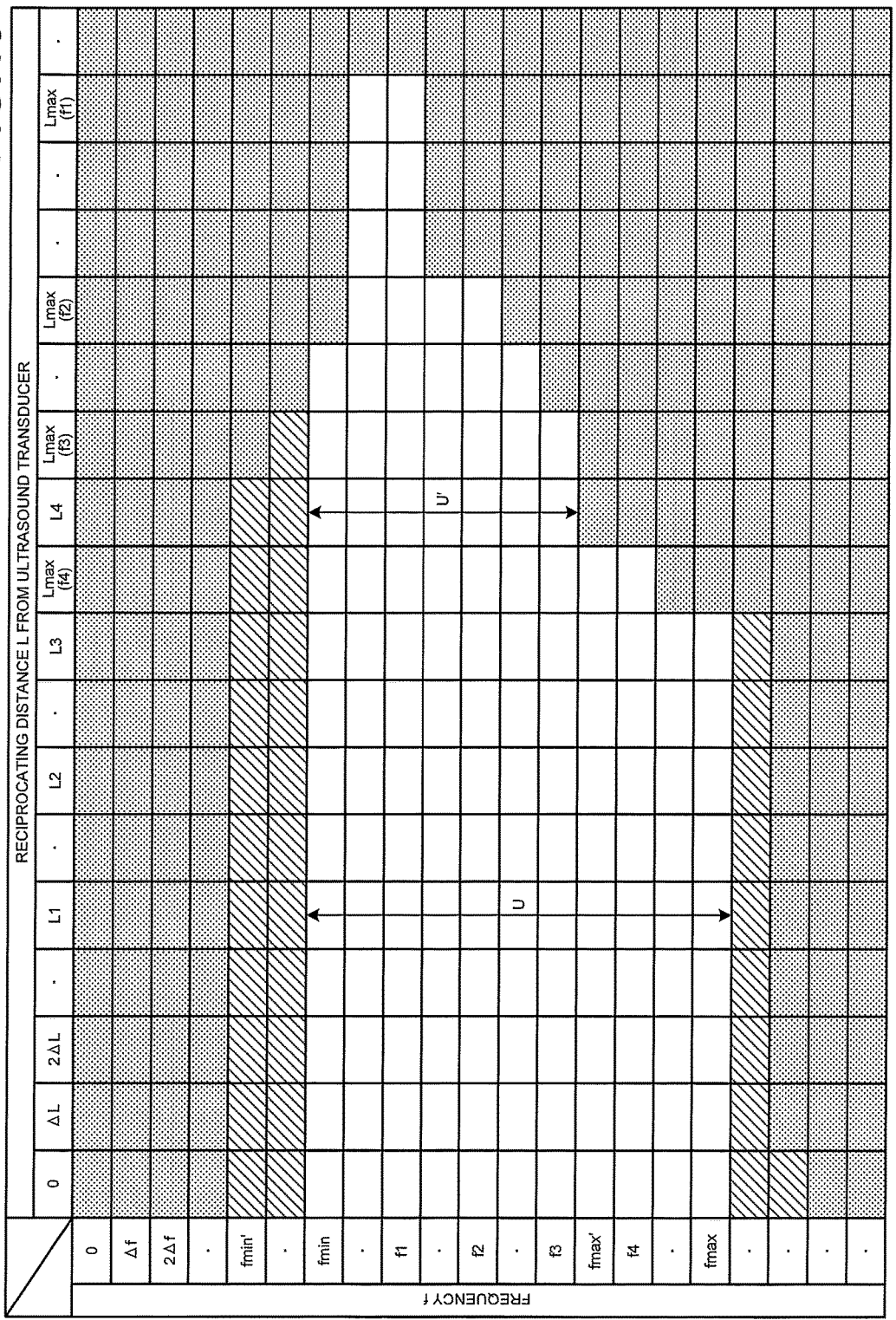
FIG. 10 is a diagram schematically illustrating frequency spectrum data that visually express a frequency band as a regression analysis target set by a band setting unit included in the ultrasound diagnosis apparatus according to the first embodiment of the present invention.

FIG. 10 is a diagram schematically illustrating a data string of the spectrum data that visually expresses a frequency band as a regression analysis target set by the band setting unit 353. In FIG. 10, description of the spectrum data F(f, L) of each of the cells is omitted. In FIG. 10, any of three different patterns is attached to the cell depending on the type of the spectrum data F(f, L). The spectrum data F(f, L) stored in a while cell indicate that the frequency f is included in the frequency band U and that the data has a value that satisfies F(f, L)>n(f, L). The spectrum data F(f, L) stored in a hatched cell indicate that the frequency f is outside the frequency band U and that the data has a value that satisfies F(f, L)>n(f, L). Furthermore, the spectrum data F(f, L) stored in a dotted cell indicate that the frequency f is outside the frequency band U and that the data has a value that satisfies F(f, L)≤n(f, L). As described above, the frequency band at the distance L=Lp (p=1, 2, and 3) is U and the frequency band at the distance L=L4 is U'. Lmax(fp) (p=1, 2, 3, and 4) illustrated in FIG. 10 will be described below.

The change rate calculation unit 354 sequentially calculates, in an order from frequency to distance, a change rate, being a number defined by the spectrum data F(f, L), for the frequency f and the distance L with respect to a linear function of the frequency f, namely, function ψ(f, L)=F(f, L)−F(f, 0).

The attenuation rate estimation unit 355 estimates an attenuation rate per unit distance and per unit frequency, of the ultrasound pulse on a scanning region using the second-order change rate calculated by the change rate calculation unit 354.

Processing performed by the change rate calculation unit 354 and the attenuation rate estimation unit 355 will be described in detail. First, a method of estimating the attenuation rate per unit distance and per unit frequency, of the spectrum data F(f, L), will be described. It is known that an acoustic pressure amplitude P(f, L) at the frequency f, of the ultrasound from the reflector existing at a distance L can be given by $$P(f,L)=P(f,0)\cdot\exp(-\mu fL) \quad (3)$$

using a positive constant μ. Since μfL>0 is established, Formula (3) indicates that the acoustic pressure amplitude P(f, L) attenuates exponentially to an increase in the frequency f and the distance L.

If an ultrasound attenuation at a frequency f in the distance section from L to L+ΔL is denoted by Loss(f, L) [dB], the attenuation is defined by $$\text{Loss}(f,L)=A\cdot\log\{P(f,L)/P(f,L+\Delta L)\}=A\cdot\log P(f,L)-A\cdot\log P(f,L+\Delta L) \quad (4),$$

where, a constant A on the right side is equal to the constant A in Formula (2). Therefore, an attenuation rate ζ per unit distance and per unit frequency can be given by the following formula, $$\zeta = \left(\frac{\partial}{\partial f}\right) \text{Lim}\{\text{Loss}(f, L)/\Delta L\} \quad (5)$$

$$= \left(\frac{\partial}{\partial f}\right)\left\{-A\left(\frac{\partial}{\partial L}\right)\log P(f, L)\right\}$$

$$= -A\left(\frac{\partial^2}{\partial f \partial L}\right)\log P(f, L)$$

where, Lim{Loss(f, L)/ΔL} indicates a limiting value at ΔL→0 in the function Loss(f, L)/ΔL. Exemplary unit of the attenuation rate ζ per unit distance and per unit frequency is [dB/cm/MHz]. Hereinafter, the attenuation rate per unit distance and per unit frequency will be referred to simply as an attenuation rate, in some cases.

Note that the relationship between the above-described constant μ and the attenuation rate ζ will be given as follows. By substituting Formula (3) into P(f, L) of Formula (5), the attenuation rate ζ is given by $$\zeta = -A\left(\frac{\partial^2}{\partial f \partial L}\right)[\log\{P(f, 0)\cdot\exp(-\mu fL)\}] \quad (6)$$

$$= -A\left(\frac{\partial^2}{\partial f \partial L}\right)\{\log P(f, 0) - \mu fL \log e\}$$

$$= (\log e)A\mu,$$

where, e is a base of natural logarithm.

In obtaining γ(f) having sensitivity of the ultrasound transducer 21 as a function of the frequency f, an amplitude component V(f, L) after completion of FFT processing on the RF data, is given by the following Formula (7).

$$V(f,L)=\gamma(f)\cdot P(f,L) \quad (7)$$

By substituting Formula (3) into P(f, L) of Formula (7), $$V(f, L) = \gamma(f)\cdot P(f, 0)\cdot\exp(-\mu fL) \quad (8)$$

$$= V(f, 0)\cdot\exp(-\mu fL)$$

is obtained.

By substituting Formula (8) in Formula (2), $$F(f, L) = A\cdot\log\{V(f, 0)\cdot\exp(-\mu fL)/V_c\} \quad (9)$$

$$= A\log\cdot\exp(-\mu fL) + A\log\{V(f, 0)/V_c\}$$

$$= -(\log e)A\mu fL + F(f, 0)$$

is obtained. Furthermore, by substituting Formula (6) into the right side of Formula (9), $$F(f,L)-F(f,0)=-\zeta fL \quad (10)$$

is derived.

By causing second order partial differential operators $\partial^2/\partial L\partial f$ and $\partial^2/\partial f\partial L$ to act on both sides of Formula (10), respectively, the following formula will be obtained.

$$\zeta = -\partial^2 F(f,L)/\partial L\partial f = -\partial^2 F(f,L)/\partial f\partial L \quad (11)$$

where $\partial^2/\partial L\partial f$ denotes prioritizing executing partial differential of the frequency f, while $\partial^2/\partial f\partial L$ denotes prioritizing executing partial differential of the distance L.

Accordingly, by calculating a second-order partial derivative $\partial^2 F(f, L)/\partial f\partial L$ or $\partial^2 F(f, L)/\partial L\partial f$ of the spectrum data F(f, L), it is possible to estimate the attenuation rate $\zeta$.

In many cases, with the above-described method of estimating the attenuation rate, it is, in practices, difficult to calculate the partial differential of the spectrum data F(f, L). The reason is, although according to the definition of partial differential, it would be necessary, in calculation of partial differential, to calculate limiting values $\Delta f \to 0$ and $\Delta L \to 0$ ($\Delta f$ and $\Delta L$ respectively denote minute displacements of f and L), the actual spectrum data F(f, L) are defined discretely, making it difficult to calculate these limiting values. To solve this issue, there is a known technique of approximating partial differential calculation of the spectrum data F(f, L) by obtaining difference among adjacent discrete values of the frequency f and the distance L. With this technique, however, partial derivative might include much noise attributable to fluctuations of the spectrum data F(f, L).

In the first embodiment, the change rate calculation unit 354 performs regression analysis on the function $\psi(f, L)=F(f, L)-F(f, 0)$ of the spectrum data F(f, L) and performs approximation using a regression line. The second-order partial derivative of this function $\psi(f, L)$ would be $$\partial^2\psi(f,L)/\partial L\partial f = \partial^2 F(f,L)/\partial L\partial f \quad (12),$$

then, by substituting Formula (11) into the right side of Formula (12), $$\partial^2\psi(f,L)/\partial L\partial f = -\zeta \quad (13)$$

is obtained. Similarly, also $$\partial^2(f,L)/\partial f\partial L = -\zeta \quad (14)$$

is obtained. Formulae (13) and (14) indicate that it is possible to calculate the attenuation rate $\zeta$ using the function $\psi(f, L)$.

The function $\psi(f, L)$ is represented as $$\psi(f,L) = -\zeta fL \quad (15)$$

using Formula (10). Approximation by the regression line is approximation by the linear function. Therefore, the closer the function approximated is to the linear function, the closer the regression line is to the function to be approximated, meaning it is possible to provide good approximation. Herein, as indicated in Formula (15), the function $\psi(f, L)$ is the linear function of the frequency f. However, the spectrum data F(f, L) is not necessarily close to the linear function of the frequency f. Therefore, in a case where a partial derivative of the function for the frequency f is approximated by a slope of the regression line of the function (namely, change rate), accuracy in approximation would be more enhanced when the function $\psi(f, L)$ is used, than the case of using the spectrum data F(f, L).

The change rate calculation unit 354 calculates, by using regression analysis, the change rate (namely, a slope of a regression line) for the frequency f of the function $\psi(f, L)$, as an approximate value of the partial derivative $\partial\psi(f, L)/\partial f$ for the frequency f of the function $\psi(f, L)$. Subsequently, the change rate calculation unit 354 calculates a change rate for the distance L (namely, a slope of a second regression line) by further performing regression analysis (second regression analysis) on the change rate for the frequency f of the function $\psi(f, L)$, and determines this value as an approximate value of the second-order partial derivative $\partial^2\psi/\partial L\partial f$. Hereinafter, an approximate value of the second-order partial derivative $\partial^2/\partial L\partial f$ will be referred to as a second-order change rate.

Processing performed by the change rate calculation unit 354 will be described more specifically. First, the change rate calculation unit 354 obtains a slope and intercept of the regression line having the frequency f of the function $\psi(f, L)$ as a variable, in a frequency band that is set by the band setting unit 353.

Figure 11:
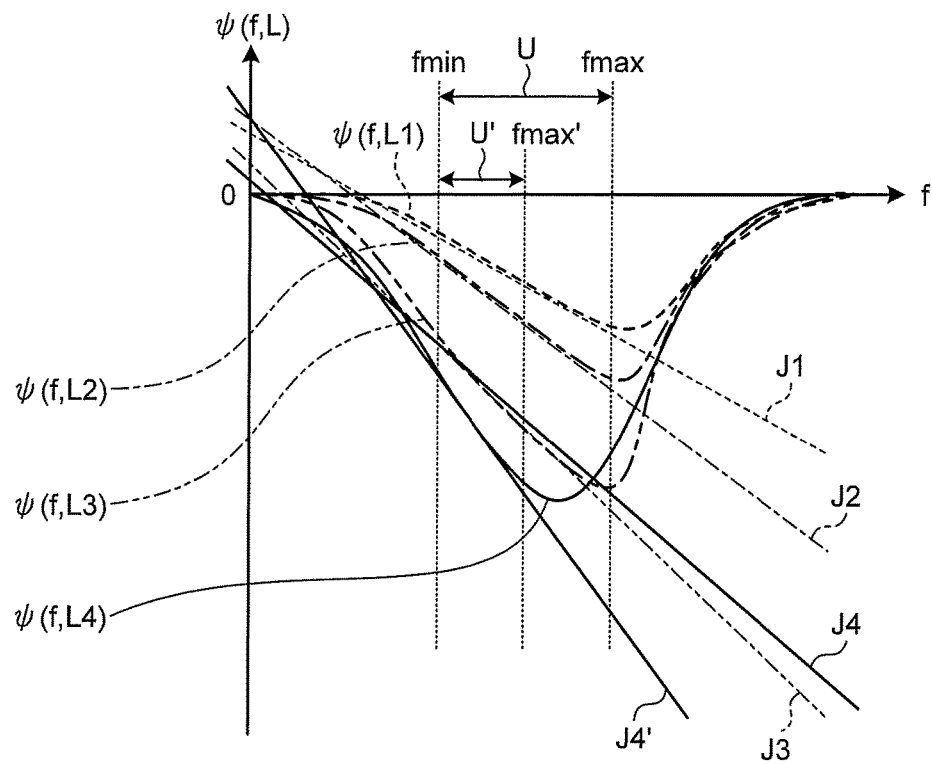
FIG. 11 is a diagram illustrating typical distance functions and a regression line for each of the functions.

FIG. 11 is a diagram illustrating a relationship between the function $\psi(f, Lp)$ and the frequency f when the distance L=Lp, as an example, and the regression line of each of the function for the frequency f (p=1, 2, 3, and 4). Regression lines J1, J2, and J3 are regression lines calculated by the change rate calculation unit 354 in performing regression analysis in the frequency band U. A regression line J4' is a regression line calculated by the change rate calculation unit 354 in performing regression analysis in the frequency band U'. For comparison, FIG. 11 also illustrates a regression line J4 calculated by the change rate calculation unit 354 performing regression analysis with the distance L=L4, in the frequency band U. Hereinafter, a slope of a regression line Jp will be defined as Sf(Lp). A slope of the regression line J4' is defined as Sf'(L4).

The slope Sf(Lp) of the regression line Jp monotonically decreases at p=1, 2, and 3, along with the increase in the distance L. In contrast, a slope Sf(L4) of the regression line J4 is greater than a slope Sf(L3) of the regression line J3 (namely, Sf(L4)>Sf(L3)). A slope Sf'(L4) of the distance L=L4 in the frequency band U' is smaller than a slope Sf(L3) of the regression line J3(Sf'(L4)<Sf(L3)). This is because, as it is clear from FIG. 8, the function $\psi(f, L4)$ takes a minimum value in the vicinity of the frequency fmax', and takes a value greater than the minimum value at the frequency fmax.

Figure 12:
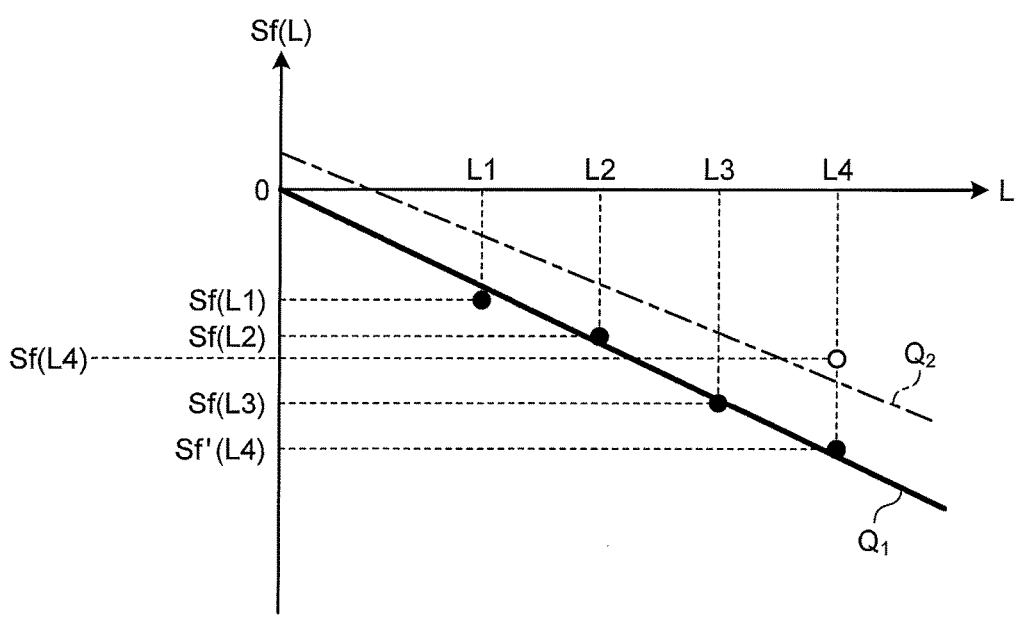
FIG. 12 is a diagram illustrating a relationship between a slope of the regression line and a distance.

Subsequently, the change rate calculation unit 354 calculates the second regression line for the distance L by performing the second regression analysis while assuming the slope Sf(L) as a function of the distance L. FIG. 12 is a diagram illustrating a relationship between the slope Sf(L) and the distance L. As described above, the change rate calculation unit 354 has calculated the exemplary slopes Sf(L1), Sf(L2), Sf(L3), and Sf'(L4) and all the other slopes. Subsequently, based on these slopes, the change rate calculation unit 354 calculates a second regression line $Q_1$ by further performing second regression analysis for the reciprocating distance L. In FIG. 12, the second regression line $Q_1$ is illustrated in a solid line. As described above, the change rate calculation unit 354 has calculated the exemplary slopes Sf(L1), Sf(L2), Sf(L3), and Sf(L4) and all the other slopes in the frequency band U. For comparison, in FIG. 12, the second regression line $Q_2$ calculated by further performing second regression analysis for the reciprocating distance L based on these slopes will be illustrated in a broken line. By comparison between the second regression lines $Q_1$, and $Q_2$, it can be seen that the second regression line $Q_1$ is better fit to the values of the slope Sf(L). As shown in Formula (15), the function $\psi(f, L)$ is a linear function of the frequency f, and in addition, in the first embodiment, the effect of noise has been removed by appropriately setting the frequency bands U and U'. Therefore, the slopes (namely, primary change rates) Sf(L1), Sf(L2), Sf(L3), and Sf'(L4) of the regression lines J1, J2, J3, and J4' respectively provide good approximation to first-order partial derivatives $\partial\psi(f, L1)/\partial f$, $\partial\psi(f, L2)/\partial f$, $\partial\psi(f, L3)/\partial f$, and $\partial\psi(f, L4)/\partial f$ of the function $\psi(f, L)$, for the frequency f. Furthermore, as shown in Formula (15), the function $\psi(f, L)$ is not only a linear function of the frequency f but also a linear function of the reciprocating distance L. Therefore, the slope (namely, second-order change rate) of the second regression line $Q_1$ provides good approximation to the partial derivative for the reciprocating distance L of the first-order partial derivative $\partial\psi(f, L)/\partial f$, that is, the second-order partial derivative $\partial^2\psi(f, L)/\partial L\partial f$ on the left side of Formula (13).

The attenuation rate estimation unit 355 calculates the attenuation rate $\zeta$ for each of sound rays of ultrasound by substituting the second-order change rate value calculated by the change rate calculation unit 354 into Formula (13). Subsequently, the attenuation rate estimation unit 355 calculates an average value of the attenuation rates $\zeta$ obtained for all the sound rays, outputs the calculation result, as an attenuation rate for the scanning region, to a combined image data generation unit 362 included in the image processing unit 36. Alternatively, the attenuation rate estimation unit 355 may determine statistics including mode, median, and a maximum value of the attenuation rate $\zeta$ for all the sound rays, as the attenuation rate of the scanning region.

The image processing unit 36 includes the B-mode image data generation unit 361 and the combined image data generation unit 362. The B-mode image data generation unit 361 generates B-mode image data that is an ultrasound image displayed by converting amplitude of an echo signal into brightness. The combined image data generation unit 362 generates combined image data by combining information on the attenuation rate $\zeta$ estimated by the attenuation rate estimation unit 355 and the B-mode image data.

The B-mode image data generation unit 361 performs signal processing using known techniques, including gain processing and contrast processing, on reception data for B-mode from the signal processing unit 34, and together with this, generates B-mode image data by performing data decimation corresponding to a data step size determined in accordance with the display range of the image on the display device 4, or by other methods. The B-mode image is a gray-scale image in which values of R (red), G (green) and B (blue), namely, variables when the RGB color system is employed as a color space, match with each other.

The B-mode image data generation unit 361 performs coordinate transformation on the reception data for B-mode so as to rearrange the scanning region to be correctly represented in space, further fills gaps among individual reception data for B-mode by performing interpolation processing for individual reception data for B-mode, and generates B-mode image data, which are digital data. The B-mode image data are digital data of the B-mode image that can represent a state of an organ within a fan-shaped scanning region illustrated in FIG. 4. The B-mode image data generation unit 361 outputs the generated B-mode image data to the combined image data generation unit 362.

The combined image data generation unit 362 generates character data indicating a value of the attenuation rate of the scanning region, and by combining the B-mode image data with the character data to be displayed adjacent to the B-mode image, generates combined image data. The combined image data generation unit 362 outputs the generated combined image data to the display device 4.

The display device 4 includes a monitor formed with liquid crystal, organic electro luminescence (EL), or the like. The display device 4 displays various types of information including a combined image corresponding to the combined image data generated by the ultrasound diagnosis apparatus 3.

Figure 13:
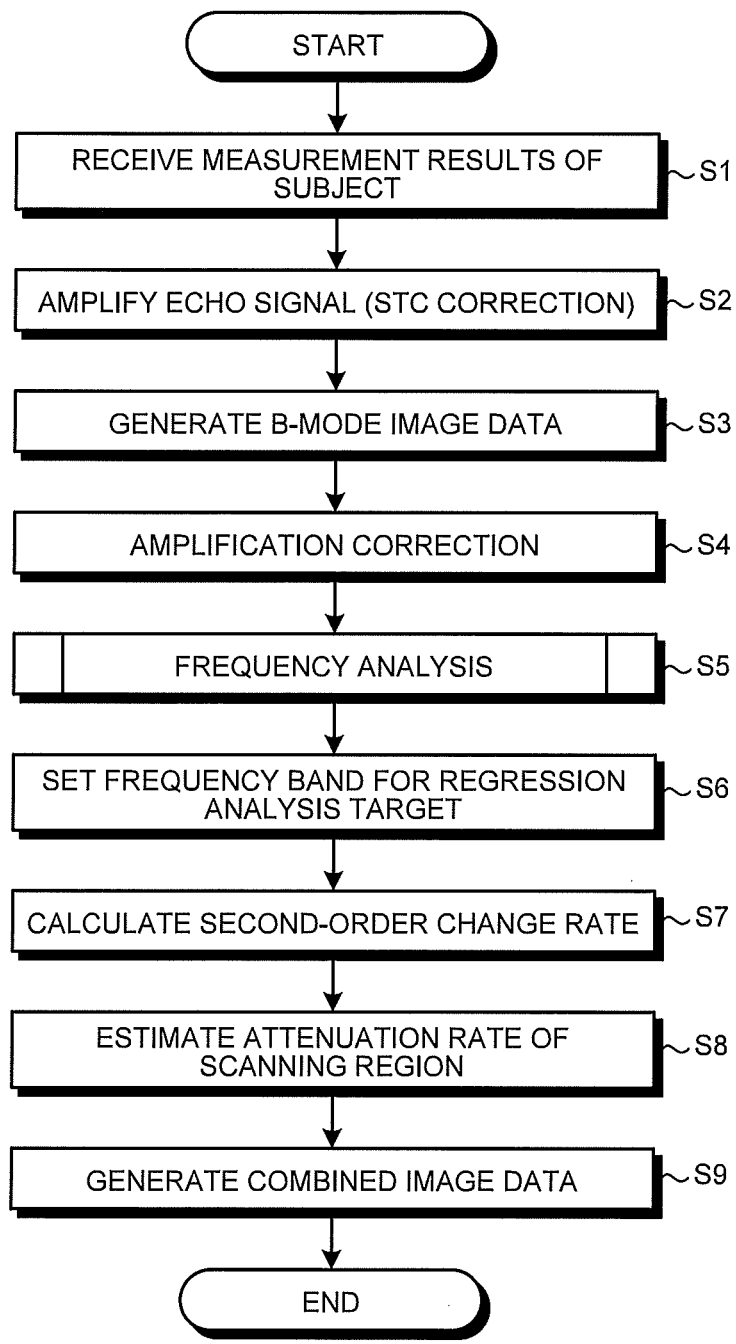
FIG. 13 is a flowchart illustrating outline of processing executed by the ultrasound diagnosis apparatus according to the first embodiment of the present invention.

FIG. 13 is a flowchart illustrating outline of processing executed by the ultrasound diagnosis apparatus 3 having the above-described configuration. Specifically, the flowchart illustrates outline of processing on and after reception of the echo signals by the ultrasound diagnosis apparatus 3 from the ultrasound endoscope 2. Hereinafter, processing performed by the ultrasound diagnosis apparatus 3 will be described with reference to FIG. 13. First, the ultrasound diagnosis apparatus 3 receives from the ultrasound endoscope 2 an echo signal as a result of measurement by the ultrasound transducer 21 (step S1).

After receiving the echo signal from the ultrasound transducer 21, the signal amplification unit 331 amplifies the echo signal (step S2). The signal amplification unit 331 performs, for example, echo signal amplification (STC correction) based on the relationship between the amplification factor and the reception depth illustrated in FIG. 3. At this time, a frequency band for various types of processing of echo signal on the signal amplification unit 331 is preferably a broad band that substantially covers a linear response frequency band for acoustic-electric conversion from an ultrasound echo to an echo signal by the ultrasound transducer 21. A purpose of this is to enable accurate approximation in approximation processing of frequency spectrum described below.

As described above, the signal amplification unit 331 amplifies the echo signal, the transmitting and receiving unit 33 generates RF data by performing filtering and A/D conversion on the amplified echo signal, and the signal processing unit 34 performs various types of processing on the RF data and generates the reception data for B-mode. The B-mode image data generation unit 361 performs appropriate coordinate transformation and interpolation processing toward the reception data for B-mode input from the signal processing unit 34, generates B-mode image data, and outputs the data to the display device 4 (step S3). The display device 4 that has received the B-mode image data displays a B-mode image corresponding to the B-mode image data.

The amplification correction unit 351 performs amplification correction on the RF data output from the transmitting and receiving unit 33 such that the amplification factor is constant regardless of the reception depth (step S4). For example, the amplification correction unit 351 performs amplification correction to achieve a relationship between the amplification factor and the reception depth, illustrated in FIG. 5.

Thereafter, the frequency analysis unit 352 calculates spectrum data (step S5) by performing frequency analysis by FFT on the RF data for individual sound rays after amplification correction. Detailed processing of step S5 will be described below.

Subsequently, the band setting unit 353 sets a frequency band for a regression analysis target (step S6). For example, in the cases illustrated in FIGS. 8 and 9, the frequency band U is set for L=L1, L2, and L3, while the frequency band U' is set for L=L4.

The change rate calculation unit 354 calculates the second-order change rate, that is, an approximate value of the second-order partial derivative $\partial^2\psi(f, L)/\partial L\partial f$ of the function $\psi(f, L)$ by performing regression analysis twice based on the frequency band set by the band setting unit 353 (step S7). For example, the change rate calculation unit 354 calculates, as the second-order change rate, slope of the regression line $Q_1$ illustrated in FIG. 12.

Thereafter, the attenuation rate estimation unit 355 estimates an attenuation rate of the ultrasound pulse in the scanning region (step S8). The attenuation rate estimation unit 355 calculates attenuation rates for each of sound rays by substituting the second-order change rate value calculated by the change rate calculation unit 354 into the left side of Formula (13). Thereafter, the attenuation rate estimation unit 355 calculates an average value of the overall calculated attenuation rates of the sound rays, and outputs the average value to the combined image data generation unit 362 as an attenuation rate of the scanning region.

Figure 14:
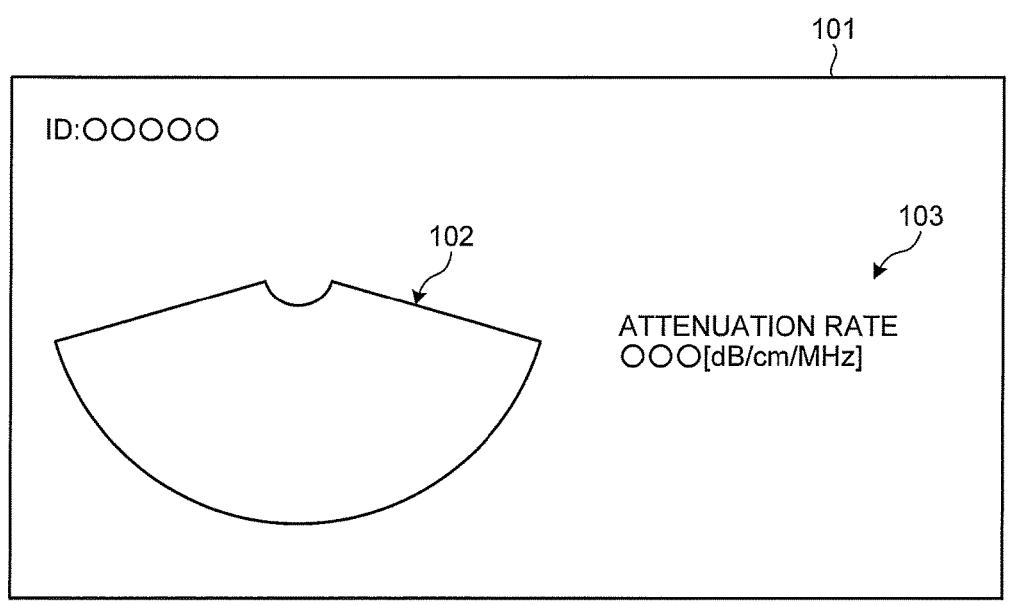
FIG. 14 is a diagram illustrating exemplary display of a combined image displayed on a display device.

The combined image data generation unit 362 generates combined image data based on the B-mode image data and the attenuation rate of the scanning region, and outputs the combined image data to the display device 4 (step S9). After receiving the combined image data, the display device 4 displays a combined image corresponding to the combined image data. FIG. 14 is a diagram illustrating exemplary display of the combined image displayed on the display device 4. A combined image 101 illustrated in FIG. 14 includes a B-mode image display section 102 and an attenuation rate display section 103. In FIG. 14, display of a specific B-mode image is omitted.

After step S9, the ultrasound diagnosis apparatus 3 finishes a series of processing. The ultrasound diagnosis apparatus 3 periodically repeats processing of steps S1 to S9.

Figure 15:
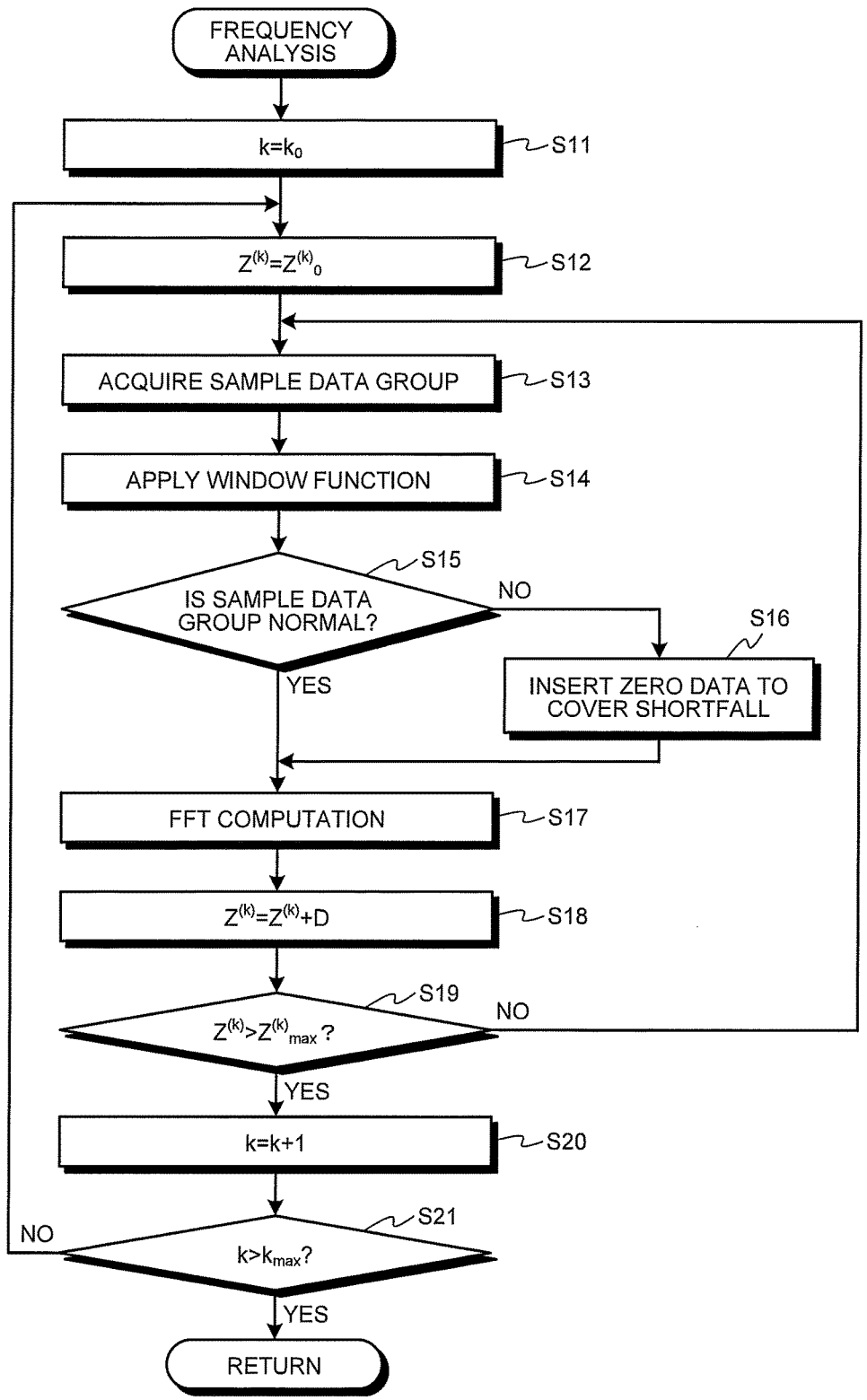
FIG. 15 is a flowchart illustrating outline of frequency analysis processing executed by the ultrasound diagnosis apparatus according to the first embodiment of the present invention.

Next, frequency analysis processing of step S5 will be described with reference to the flowchart in FIG. 15 First, the frequency analysis unit 352 sets a counter k for identifying a sound ray as an analysis target, to $k_0$ (step S11). This initial value $k_0$ is either a value that has been arbitrarily input by indication by a user via the input unit 37, or a value that has been preset on the storage unit 32.

Subsequently, the frequency analysis unit 352 sets (step S12) an initial value $Z^{(k)}_0$ of a data position (corresponding to reception depth) $Z^{(k)}$, representing a series of data group (sample data group) generated for FFT calculation as described above. For example, FIG. 6 illustrates a case, as described above, where a first data position of a sound ray $SR_k$ has been set as the initial value $Z^{(k)}_0$.

Thereafter, the frequency analysis unit 352 acquires a sample data group (step S13), and applies a window function stored in the storage unit 32 to the acquired sample data group (step S14). By applying the window function to the sample data group in this manner, it is possible to avoid discontinuity of the sample data group on a border and prevent occurrence of artifacts. The window function applied in step S14 is any of Hamming, Hanning, Blackman, or the like, and is pre-stored in the storage unit 32.

Subsequently, the frequency analysis unit 352 determines whether the sample data group of the data position $Z^{(k)}$ is a normal data group (step S15). As discussed with reference to FIG. 6, it is necessary that the sample data group has the number of data that is power of two. Hereinafter, the number of data of the sample data group is determined to be $2^n$ (n: positive integer). Setting in the first embodiment is performed such that the data position $Z^{(k)}$ may be arranged at a center of the sample data group to which $Z^{(k)}$ belongs, as much as possible. Specifically, since the number of data of the sample data group is $2^n$, $Z^{(k)}$ is set to a $2^n/2$ (=$2^{n-1}$) th position close to the center of the sample data group. In this case, the sample data group being normal means that data having the number of $2^{n-1}-1$ (=N) exist on a side shallower than the data position $Z^{(k)}$, and that the data having the number of $2^{n-1}$ (=M) exist on a side deeper than the data position $Z^{(k)}$. In the case illustrated in FIG. 6, the sample data group $F_j$ (j=1, 2, ..., K-1) is normal. Note that FIG. 6 exemplifies a case of n=4 (N=7 and M=8).

In a case where the result of determination in step S15 indicates that the sample data group of the data position $Z^{(k)}$ is normal (step S15: Yes), the frequency analysis unit 352 moves on to step S17 described below.

In a case where the result of determination in step S15 indicates that the sample data group of the data position $Z^{(k)}$ is not normal (step S15: No), the frequency analysis unit 352 generates a normal sample data group (step S16) by inserting zero data to cover the shortfall. The sample data group determined to be not normal in step S15 (e.g., sample data group $F_K$ in FIG. 6) has undergone action of the window function before addition of the zero data. Therefore, insertion of zero data to the sample data group would not cause discontinuity of data. After step S16, the frequency analysis unit 352 moves on to step S17 to be described below.

In step S17, the frequency analysis unit 352 obtains spectrum data as frequency distribution of amplitude by performing FFT computation using the sample data group (step S17). As a result, spectrum data illustrated in individual columns in FIG. 7 are obtained.

Subsequently, the frequency analysis unit 352 changes the data position $Z^{(k)}$ by a step size D (step S18). The step size D is assumed to be pre-stored in the storage unit 32. FIG. 6 illustrates an exemplary case of D=15. An interval $\Delta L$ of the reciprocating distance L illustrated in FIG. 7 is defined as twice the value (=sampling size×D) used for conversion from the step size D into the distance. Accordingly, determination of the step size D can uniquely define the interval $\Delta L$. The step size D is desirably equal to the data step size used in generation of B-mode image data by the B-mode image data generation unit 361. However, when reduction of calculation on the frequency analysis unit 352 is desired, a greater value than the data step size may be set as the step size D.

Thereafter, the frequency analysis unit 352 determines (step S19) whether the data position $Z^{(k)}$ is greater than a maximum value $Z^{(k)}_{max}$ in the sound ray $SR_k$. In a case where the data position $Z^{(k)}$ is greater than the maximum value $Z^{(k)}_{max}$ (step S19: Yes), the frequency analysis unit 352 increments the counter k by one (step S20). This means transition of processing to an adjacent sound ray. In contrast, in a case where the data position $Z^{(k)}$ is equal to or less than the maximum value $Z^{(k)}_{max}$ (step S19: No), the frequency analysis unit 352 returns to step S13.

After step S20, the frequency analysis unit 352 determines whether the counter k is greater than the maximum value $k_{max}$ (step S21). If the counter k is greater than $k_{max}$ (step S21: Yes), the frequency analysis unit 352 finishes a series of frequency analysis processing. In contrast, the counter k is equal to or less than $k_{max}$ (step S21: No), the frequency analysis unit 352 returns to step S12. This maximum value $k_{max}$ is either a value that has been arbitrarily input by indication by a user via the input unit 37, or a value that has been preset on the storage unit 32.

In this manner, the frequency analysis unit 352 performs a plurality of times of FFT calculations for individual sound rays having the number ($k_{max}-k_0+1$) within a region of interest.

According to the first embodiment of the present invention described above, the attenuation rate of an ultrasound signal per unit distance and per unit frequency, in a scanning region of the ultrasound transducer is estimated by using the second-order change rate obtained by calculating the distance change rate and the frequency change rate in this order in the function defined using the frequency spectrum. With this procedure, it is possible to calculate the attenuation rate of the ultrasound accurately and easily, and to enhance reliability of an image based on the attenuation rate.

According to the first embodiment, it is not necessary to obtain sound velocity as in JP 2010-82230 A, and the transmission waveform is not assumed to be a Gaussian shape. Therefore, it is possible to calculate the attenuation rate accurately. Note that the second-order change rate in the first embodiment is the second-order change rate of the function of the frequency and the distance (or reception depth) and completely differs from "second-order change rate of a phase" in JP 2010-82230 A described above. This also applies to second and third embodiments described below.

According to the first embodiment, the frequency band as a calculation target is set by comparison with the noise level data corresponding to the spectrum data, and thus, it is possible to calculate the attenuation rate uniquely in a region that has a sufficiently high S/N and is effective for estimating the attenuation rate. With this configuration, it is possible to calculate the attenuation rate with high accuracy and to enhance reliability of an image based on the attenuation rate.

According to the first embodiment, it is not necessary to perform complicated processing such as manually specifying a region within an image. Accordingly, it is possible to easily calculate the attenuation rate.

According to the first embodiment, linear regression analysis is used, and thus, it is possible to easily calculate the frequency change rate and the distance change rate.

According to the first embodiment, the function $\psi(f, L)$ of the spectrum data, as a linear function of frequency, is used. Accordingly, it is possible to enhance accuracy of approximation using the slope of the regression line.

According to the first embodiment, the noise level data storage unit stores noise level data corresponding to the ultrasound transducer for each of a plurality of types or devices. Therefore, it is possible to calculate accurately the attenuation rate of the ultrasound for all connectable ultrasound transducers.

Alternatively, in the first embodiment, it is allowable to configure that the comparison unit 353a does not compare the spectrum data F(f, L) with the noise level data n(f, L) itself, but there may be provided a margin instead of linear function $a \cdot n(f, L) + b$ ($a \geq 1$, $b \geq 0$; a, b: constant) of the noise level data n(f, L). In this case, it is possible to further reduce the effect of noise on the second-order change rate calculated by the change rate calculation unit 354 and on the attenuation rate estimated by the attenuation rate estimation unit 355, and to further enhance accuracy in calculating the attenuation rate.

In view of the fact that a low S/N typically occurs on the side of high frequency on which attenuation depending on the frequency is severe, it is allowable to configure such that, when the band setting unit 353 sets a frequency band as a regression analysis target, the minimum frequency is fixed with an initial value fmin, while the maximum frequency value is changed in the range of f>fmin, from the initial value fmax. In this case, by excluding the high-frequency side on which attenuation is severe when the change rate calculation unit 354 and the attenuation rate estimation unit 355 perform calculation, it is possible to enhance accuracy in estimating attenuation rate.

Alternatively, it is allowable to configure such that the ultrasound diagnosis apparatus 3 estimates the attenuation rate of a partial region of the scanning region instead of estimating the attenuation rate of the scanning region. In this case, the region may preferably be set by the user via the input unit 37.

Second Embodiment

In a second embodiment of the present invention, a method for calculating the second-order change rate performed by the change rate calculation unit of the ultrasound diagnosis apparatus differs from the method in the first embodiment. The ultrasound diagnosis apparatus according to the second embodiment has a configuration similar to the configuration of the ultrasound diagnosis apparatus 3 described in the first embodiment.

In the second embodiment, the change rate calculation unit 354 first calculates a change rate of the spectrum data F(f, L) with respect to the distance L using regression analysis and determines the calculated value as an approximate value of a partial derivative $\partial \psi(f, L)/\partial L$. Thereafter, the change rate calculation unit 354 calculates a change rate of the partial derivative $\partial F(f, L)/\partial L$ for the frequency f using the second regression analysis, thereby calculating an approximate value of the second-order partial derivative $\partial^2 F(f, L)/\partial f \partial L$, namely, the second-order change rate.

In this case, since the spectrum data F(f, 0) for distance L=0 is not a function of the distance L, $\partial F(f, L)/\partial L = \partial \psi(f, L)/\partial L$ is established. Therefore, in the second embodiment, the change rate calculation unit 354 does not need to calculate the function $\psi(f, L)$, but is able to calculate the second-order change rate from the spectrum data F(f, L).

The change rate calculation unit 354 extracts a regression analysis limit Lmax(f) per frequency f. The regression analysis limit Lmax(f) is a maximum value of the distance L on the frequency f. In the data strings of the spectrum data illustrated in FIG. 10, the regression analysis limit Lmax(fp) corresponding to each of the frequency f=fp (p=1, 2, 3, and 4) is illustrated. In the case illustrated in FIG. 10, the regression analysis limit Lmax(fp) corresponds to a value of the distance L included in the right-end cell on a distribution range of the white cell on the frequency fp.

Figure 16:
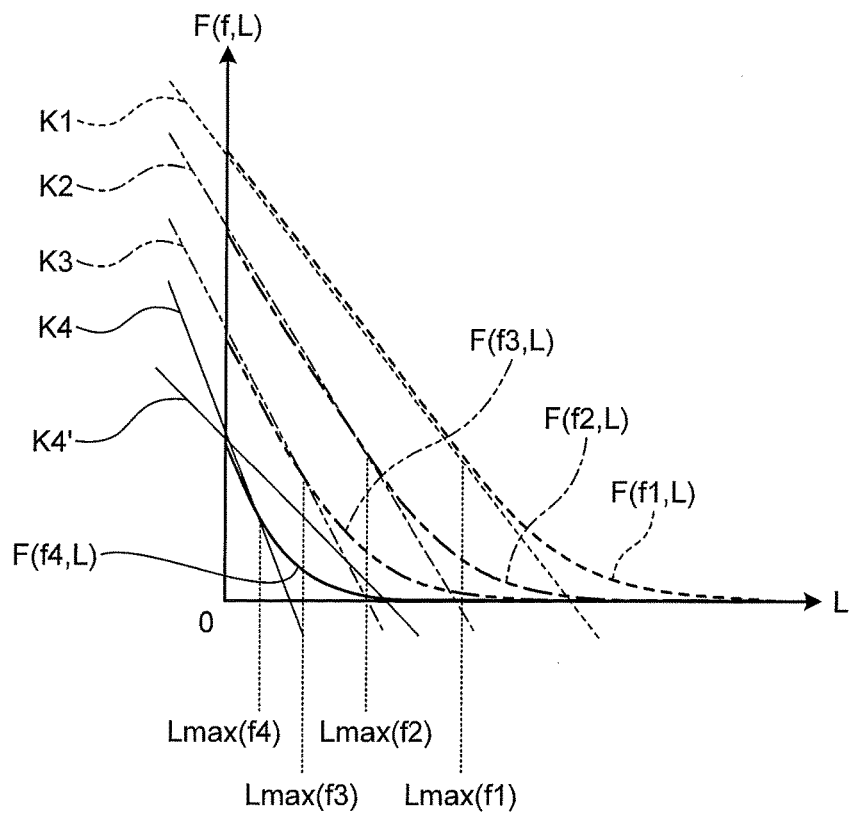
FIG. 16 is a diagram illustrating a relationship between data of a frequency spectrum with a constant frequency, and the distance.

The change rate calculation unit 354 executes regression analysis of the spectrum data F(f, L) for the distance L and calculates the slope SL(f) of the regression line in the distance section $0 \leq L \leq Lmax(f)$. FIG. 16 is a diagram illustrating a relationship between the spectrum data F(f, L) and the distance L when the frequency f is constant. Specifically, the figure illustrates a relationship between each of spectrum data F(f, L1), F(f, L2), F(f, L3), and F(f, L4) on four mutually different distances, and the distance L. Here, the frequency fp is a constant satisfying 0<f1<f2<f3<f4. As illustrated in FIG. 16, on the spectrum data F(f, L), the larger the frequency f, the severer the attenuation along with the increase in the distance L because of an effect of frequency-dependent attenuation at propagation of the ultrasound within the subject. Note that, although in FIG. 16 only four representative spectrum data are illustrated as in FIG. 8, more spectrum data F(f, L) than this example may be calculated in general.

FIG. 16 illustrates a regression line Kp of the spectrum data F(fp, L) in the distance section $0 \leq L \leq Lmax(fp)$. The spectrum data F(fp, L) appears substantially linear from L=0 until the regression analysis limit Lmax(fp) is reached. This linearity, however, is disturbed after exceeding the regression analysis limit Lmax(fp) due to the effect of noise and the effect generated by attenuation of the spectrum data F(fp, L) itself to reach a level close to zero.

The higher the frequency f, the steeper the slope of the regression line Kp becomes, due to the effects of frequency-dependent attenuation. In other words, when the slope of the regression line Kp is defined as SL(fp), SL(f1)>SL(f2)>SL(f3)>SL(f4) is established.

For comparison, calculating of a regression line using the regression analysis limit Lmax(f1) of the lowest frequency f1 among the four frequencies, for four spectrum data F(fp, L) illustrated in FIG. 16 will be discussed. FIG. 16 illustrates, as an example, a regression line K4' calculated when the regression analysis limit Lmax(f1) is applied to the spectrum data F(f4, L). A slope SL'(f4) of the regression line K4' is greater than the slope SL(f4), that is, SL'(f4)>SL(f4) is established because the spectrum data F(f4, L) fall to the noise level in the vicinity of L=Lmax(f4). In cases of p=1, 2, and 3, similar relationships are established although not illustrated.

Figure 17:
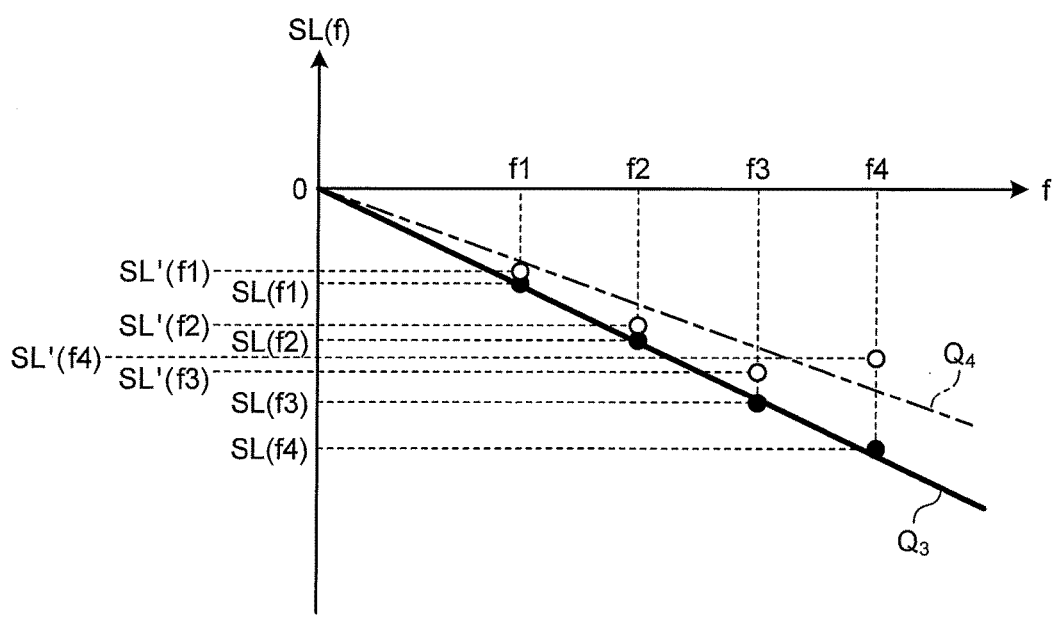
FIG. 17 is a diagram illustrating a relationship between a slope of a regression line for the data of frequency spectrum, and the frequency.

The change rate calculation unit 354 calculates a second regression line for the frequency f by performing second regression analysis having the slope SL(f) as a function of the frequency f. FIG. 17 is a diagram illustrating a relationship between the slope SL(f) and the frequency f. In FIG. 17, the black dots indicate the relationship between the slope SL(fp) and the frequency fp calculated by the change rate calculation unit 354 in performing regression analysis of the spectrum data F(fp, L) in the distance section 0≤L≤Lmax(fp). In contrast, the white dots are data for comparison and indicate the relationship between the slope SL'(fp) of the regression line Kp' and the frequency fp, calculated by the change rate calculation unit 354 in performing regression analysis of the spectrum data F(fp, L) in the distance section 0≤L≤Lmax(f1).

As described above, the change rate calculation unit 354 calculates the exemplary slopes SL(f1), SL(f2), SL(f3), and SL(f4), and all the other slopes, in the distance section 0≤L≤Lmax(f). Based on the slopes, the change rate calculation unit 354 further performs the second regression analysis for the frequency f, thereby calculating a second regression line $Q_3$. The second regression line $Q_3$ is illustrated in a solid line in FIG. 17. For comparison, the change rate calculation unit 354 calculates the slopes SL'(f1), SL'(f2), SL'(f3), and SL'(f4), and all the other slopes, in a tentative distance section 0≤L≤Lmax(f1), and based on these slopes, performs the second regression analysis for the frequency f. A second regression line $Q_4$ for this case is illustrated in a broken line in FIG. 17. By comparing the second regression lines $Q_3$ and $Q_4$, it can be seen that the second regression line $Q_3$ is better fit to the value of the slope SL(f). The slope of the second regression line $Q_3$ provides an approximate value for a second-order partial derivative $\partial^2\psi(f, L)/\partial f \partial L$ on the left side of Formula (14), namely, the second-order change rate.

According to the second embodiment of the present invention described above, the attenuation rate of an ultrasound signal per unit distance and per unit frequency, in a scanning region of the ultrasound transducer is estimated using the second-order change rate obtained by calculating the frequency change rate and the distance change rate, in this order, on the frequency spectrum. With this configuration, it is possible, similarly to the first embodiment, to calculate the attenuation rate of the ultrasound accurately and easily, and to enhance reliability of an image based on the attenuation rate.

In the second embodiment, regression analysis for the distance is executed prior to the regression analysis for the frequency. This enables regression analysis to be performed on the spectrum data as they are, making it possible to reduce computational complexity.

Third Embodiment

Figure 18:
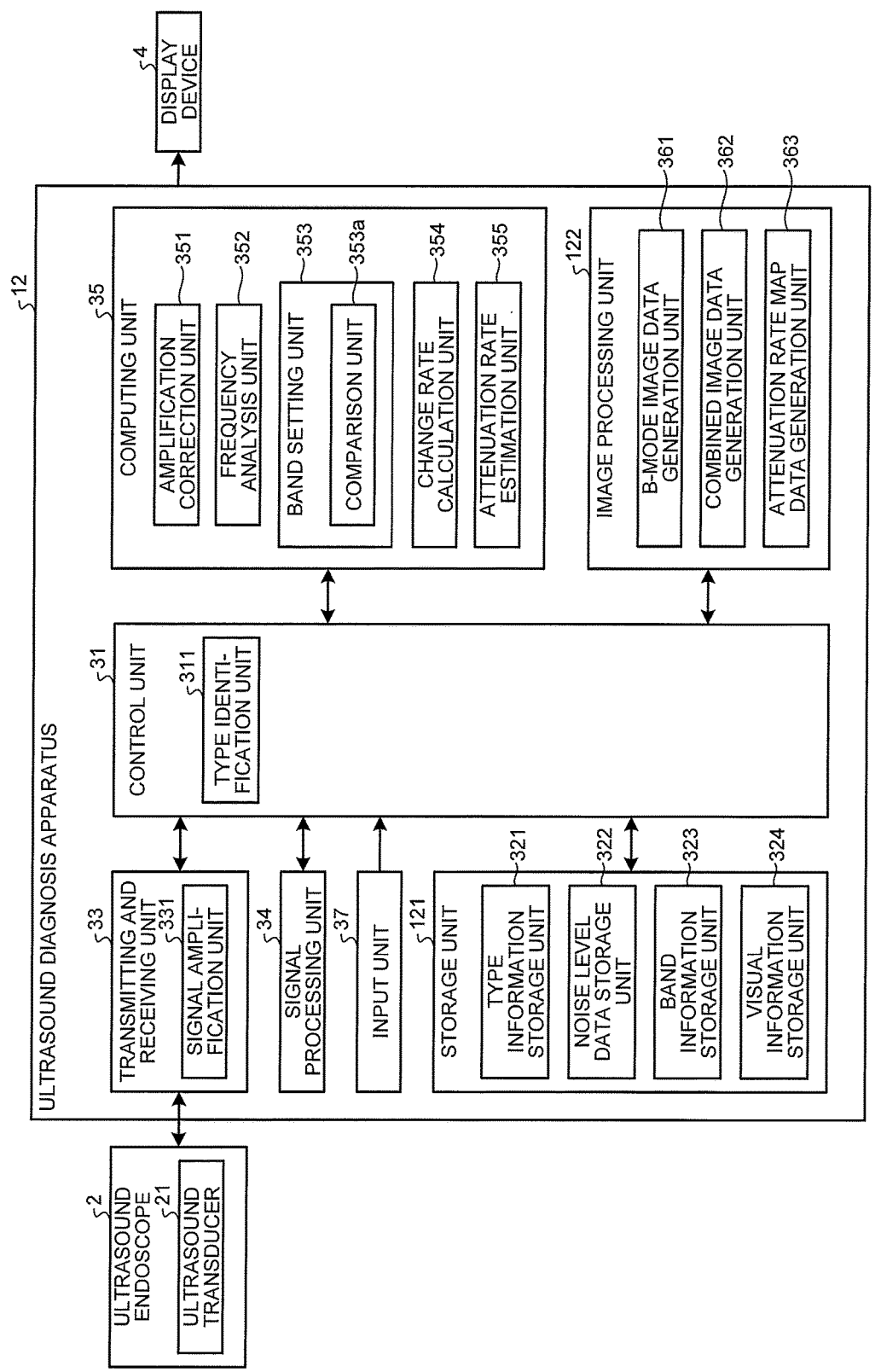
FIG. 18 is a block diagram illustrating a functional configuration of an ultrasound diagnosis system according to a third embodiment of the present invention.

FIG. 18 is a block diagram illustrating a functional configuration of an ultrasound diagnosis system according to a third embodiment of the present invention. An ultrasound diagnosis system 11 illustrated in FIG. 18 includes the ultrasound endoscope 2, an ultrasound diagnosis apparatus 12, and the display device 4.

In the ultrasound diagnosis apparatus 12, configurations of a storage unit 121 and an image processing unit 122 differ from the storage unit 32 and the image processing unit 36 in the ultrasound diagnosis apparatus 3, respectively.

The storage unit 121 includes the type information storage unit 321, the noise level data storage unit 322, the band information storage unit 323, and in addition to these, includes a visual information storage unit 324 configured to store visual information attached to an image according to an attenuation rate value. Herein, the visual information may be any of luminance, hue, brightness, and saturation, with any of which a value corresponding to the attenuation rate value is associated. The visual information storage unit 324 may be configured to store a plurality of types of visual information in association with the attenuation rate. In this case, it is only required to configure to allow the user to select desired visual information via the input unit 37.

The image processing unit 122 includes an attenuation rate map data generation unit 363, in addition to the B-mode image data generation unit 361 and the combined image data generation unit 362. The attenuation rate map data generation unit 363 generates attenuation rate map data by attaching the visual information according to the attenuation rate value estimated by the attenuation rate estimation unit 355, to the image, with reference to the visual information storage unit 324.

Figure 19:
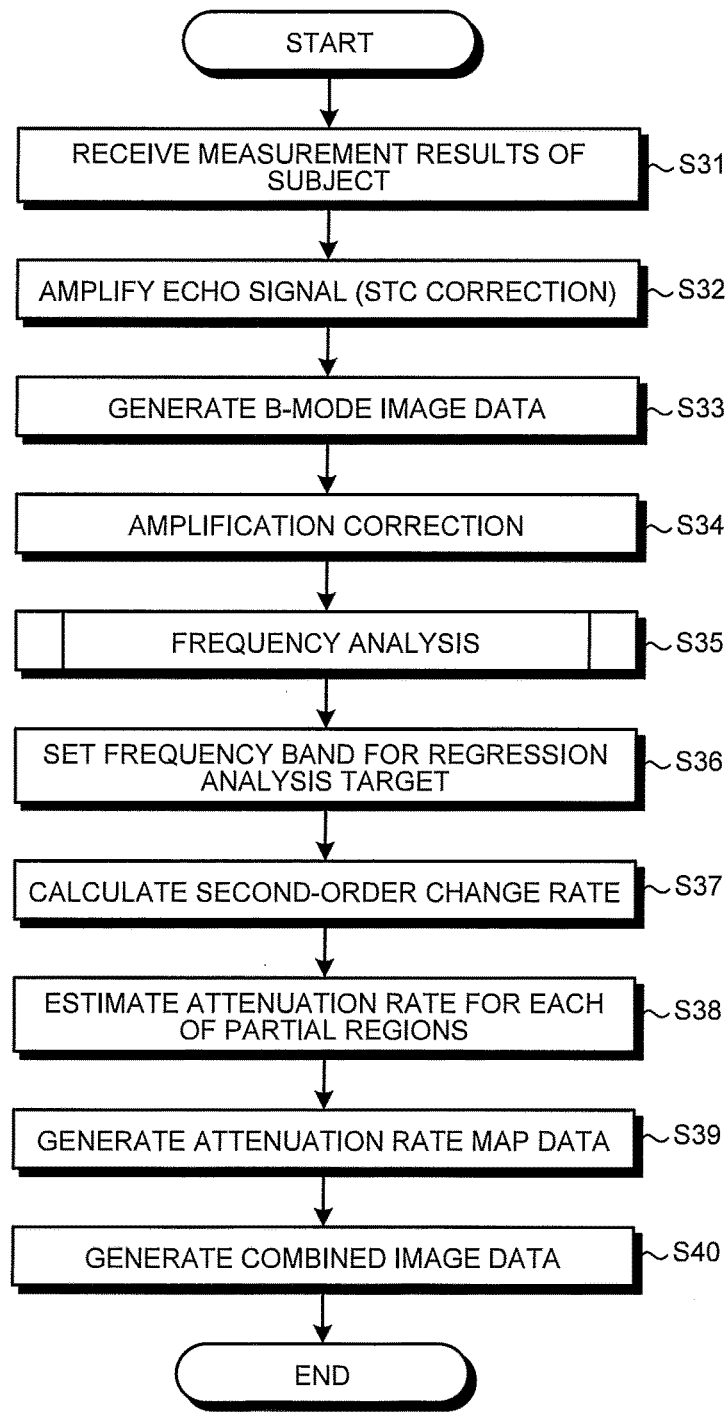
FIG. 19 is a flowchart illustrating outline of processing executed by an ultrasound diagnosis apparatus according to the third embodiment of the present invention.

FIG. 19 is a flowchart illustrating outline of processing executed by the ultrasound diagnosis apparatus 12 having the above-described configuration. Specifically, the flowchart illustrates outline of processing on and after reception of the echo signals by the ultrasound diagnosis apparatus 12 from the ultrasound endoscope 2. Steps S31 to S36 in FIG. 19 correspond to steps S1 to S6 in FIG. 13, respectively. Hereinafter, processing after step S36 will be described.

After step S36, the change rate calculation unit 354 calculates second-order change rate of spectrum data (step S37). At this time, the change rate calculation unit 354 calculates the second-order change rate for each of a plurality of partial regions, pre-divided and preset within a scanning region. Note that, in the third embodiment, the calculation order of the frequency change rate and the distance change rate, at the time of calculation of the second-order change rate by the change rate calculation unit 354, is not particularly limited.

Figure 20:
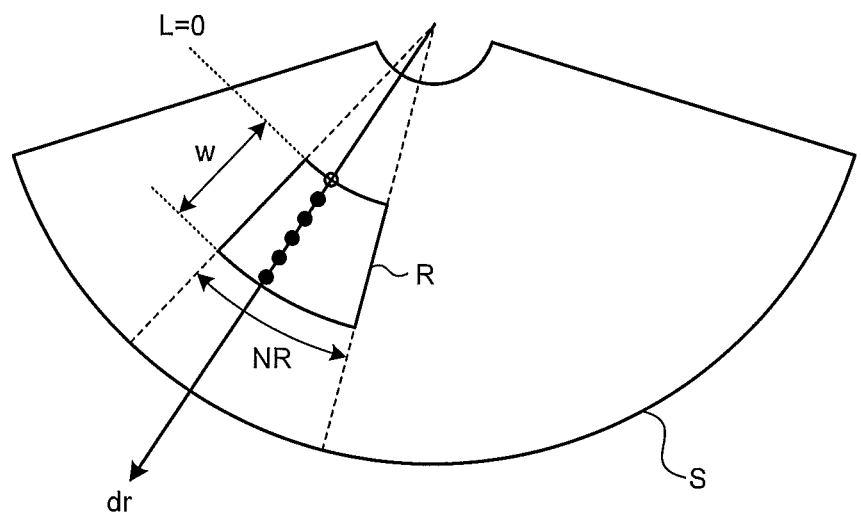
FIG. 20 is a diagram illustrating an exemplary setting of a partial region in a scanning region of an ultrasound transducer.

FIG. 20 is a diagram schematically illustrating a setting example of the partial region. A partial region R in FIG. 20 is a fan-shaped region having a length (depth range) w in the depth direction and NR sound rays. In a scanning region S, transmission-reception directions are divided by the depth range w, with the scanning direction being divided for each of the NR sound rays. In FIG. 20, among a plurality of transmission-reception directions within the scanning region S, spectrum data within the partial region R among the spectrum data calculated on a transmission-reception direction dr are indicated by black dots, while spectrum data located on a border of the partial regions R are indicated by white dots.

The change rate calculation unit 354 determines a reference position (position where the distance is zero) of the distance of the spectrum data in the partial region R as a position closest to the surface of the ultrasound transducer 21 within the partial region R, and obtains a value (2z') that is twice the difference z' in depth from this reference position, and then, performs calculation using this 2z' as a new distance. In a case where the reference position of the partial region R when the surface of the ultrasound transducer 21 is determined as the reference position of distance is L=Lmin, the spectrum data at the white dots positions described above would be represented as F(f, Lmin). The change rate calculation unit 354 may calculate the second-order change rate in the partial region R by using the spectrum data F(f, Lmin) instead of the spectrum data F(f, 0) in Formula (10).

Using a result of calculation by the change rate calculation unit 354, the attenuation rate estimation unit 355 estimates, for a plurality of partial regions included in the scanning region, an attenuation rate for the partial region (step S38). First, the attenuation rate estimation unit 355 calculates an attenuation rate for each of the sound rays using all the second-order change rates calculated in the partial regions. Thereafter, the attenuation rate estimation unit 355 calculates an average value of the attenuation rate obtained for all the sound rays, calculated in a same partial region, and outputs the average value to the attenuation rate map data generation unit 363 as an estimated value of the attenuation rate for the corresponding partial region. Alternatively, the attenuation rate estimation unit 355 may determine statistics including mode, median, and a maximum value of the attenuation rate for all the sound rays calculated in the same partial region, as the attenuation rate of the corresponding partial region.

Thereafter, the attenuation rate map data generation unit 363 generates attenuation rate map data by allocating visual information corresponding to the attenuation rate of each of the partial regions to each of the partial regions with reference to the visual information storage unit 324, and then, outputs the generated attenuation rate map data to the combined image data generation unit 362 (step S39). It is also allowable that the combined image data generation unit 362 generates combined image data that further displays the estimated value for the attenuation rate for each of the partial regions, as textual information.

Figure 21:
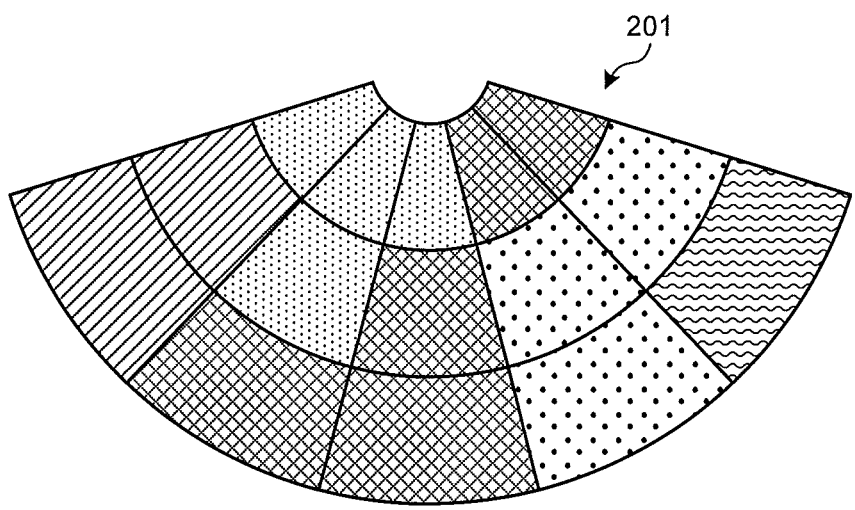
FIG. 21 is diagram illustrating exemplary display of a combined image with attenuation rate map data displayed on the display device.

The combined image data generation unit 362 generates the combined image data by superposing the attenuation rate map data on the B-mode image data, and outputs the combined image data to the display device 4 (step S40). After receiving the combined image data, the display device 4 displays a combined image corresponding to the combined image data. FIG. 21 is diagram illustrating exemplary display of a combined image with attenuation rate map data displayed on the display device 4. In a combined image 201 illustrated in FIG. 21, different visual information is allocated for each of the regions. In FIG. 21, the visual information is illustrated schematically with patterns. In FIG. 21, to simplify description, specific display of the B-mode image is omitted.

In the third embodiment, it would be preferable that an exemplary depth range w is approximately 1 cm. In a case where the depth range w is approximately 1 cm, it is desirable that the range ΔL of the section removed as the RF data when the frequency analysis unit 352 performs the FFT processing would be approximately 2 mm. At this time, the range Δz'(=ΔL/2) of the depth z' of the reference position corresponding to the interval ΔL would be approximately 1 mm.

According to the third embodiment of the present invention described above, the attenuation rate of an ultrasound signal per unit distance and unit frequency in a scanning region of the ultrasound transducer is estimated by using the second-order change rate obtained by calculating, in a predetermined order, the frequency spectrum or the distance change rate and the frequency change rate in the function defined using the frequency spectrum. With this procedure, similarly to the first and second embodiments, it is possible to calculate the attenuation rate of the ultrasound accurately and easily, and to enhance reliability of an image based on the attenuation rate.

According to the third embodiment, the scanning region of the ultrasound transducer is divided into a plurality of partial regions. By calculating the statistics of the attenuation rate obtained on each of the partial regions, estimation of the attenuation rate for each of the partial regions is performed. Thereafter, the attenuation rate map data is generated by attaching visual information according to the value of the attenuation rate in each of the partial regions. As a result, it is possible to provide information that makes it easier for the user to grasp distribution of the attenuation rate.

In the third embodiment, it is also allowable to set adjacent fan-shaped regions to be arranged to mutually overlap, among the fan-shaped regions, each of which is a minimum unit of the attenuation rate map.

In the third embodiment, it is also allowable to perform calculation of the attenuation rate of each of the fan-shaped regions in parallel, instead of performing it in sequence.

It is also allowable in the third embodiment, that the combined image data are generated in a manner such that one fan-shaped region is set as a region of interest (ROI) based on a setting signal received by the input unit 37, and that the values of the attenuation rate within the region of interest are further combined.

Other Embodiments

Embodiments of the present invention have been described hereinabove, however, the present invention is not intended to be limited to the above-described first to third embodiments. For example, the ultrasound diagnosis apparatus can be configured by connecting circuits having individual functions via a bus, or can be configured such that a part of the function is incorporated into a circuit structure of another function. Specifically, functions of the change rate calculation unit may be incorporated into a circuit having a function of the attenuation rate estimation unit.

An ultrasound miniature probe that has a small diameter and has no optical system may be employed as the ultrasound probe. In typical cases, the ultrasound miniature probe is inserted into biliary tract, bile duct, pancreatic duct, trachea, bronchus, urethra, and ureter, and is applicable to the observation of the surrounding organs (pancreas, lung, prostate gland, bladder, and lymph nodes, or the like).

An external ultrasound probe that emits ultrasound from the surface of the subject may also be employed as the ultrasound probe. The external ultrasound probe is typically used to observe abdominal organs (liver, gall bladder, and bladder), breast (mammary gland, in particular), and the thyroid.

The ultrasound transducer may be any of a linear transducer, radial transducer, and a convex transducer. In a case where the ultrasound transducer is a linear transducer, the scanning region has a quadrangular shape (rectangle or square). In a case where the ultrasound transducer is a radial transducer or a convex transducer, the scanning region is fan-shaped or circular.

According to some embodiments, it is possible to calculate an attenuation rate of ultrasound accurately and easily and to enhance reliability of images based on the attenuation rate.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound diagnosis apparatus comprising: a processor comprising hardware, wherein the processor is configured to:
   analyze a frequency of an ultrasound signal obtained by an ultrasound probe comprising an ultrasound transducer configured to transmit ultrasound to a subject and receive the ultrasound reflected from the subject, thereby to calculate a frequency spectrum of the ultrasound signal for each reception depth;
   calculate, in a predetermined order, a distance change rate and a frequency change rate in the frequency spectrum or in a function defined by using the frequency spectrum, thereby to calculate a second-order change rate of the frequency spectrum or of the function;
   estimate an attenuation rate of the ultrasound signal, per unit distance and per unit frequency, in a predetermined region within a scanning region of the ultrasound transducer using the second-order change rate; and
   generate an ultrasound image based on the ultrasound signal, and perform image processing on the ultrasound image based on the attenuation rate,
   wherein the attenuation rate is estimated based on an equation:

$$\partial 2\psi(f,L)/\partial L \partial f = -\zeta$$

where $\zeta$ is the attenuation rate,
   by using a function:

$$\psi(f,L) = F(f,L) - F(f,0)$$

wherein the right side of the equation can be replaced with $\partial 2\psi(f, L)/\partial f \partial L$ obtained by a procedure comprising:
   (i) in a possible range of a reciprocating distance (L), a slope (the frequency change rate) of a regression line of the frequency f of the function $\psi(f, L)$, the slope being an approximate value of $\partial \psi(f, L)/\partial f$;
   (ii) a slope (the distance change rate) of a regression line for the reciprocating distance L of the approximate values of $\partial \psi(f, L)/\partial f$ is obtained, the slope being an approximate value of $\partial 2\psi(f, L)/\partial f \partial L$; and
   (iii) the approximate value of $\partial 2\psi(f, L)/\partial f \partial L$ is multiplied by $-1$ to obtain an approximate value of the attenuation rate $\zeta$ as represented by the equation.

2. The ultrasound diagnosis apparatus according to claim 1,
   wherein the processor is configured to:
   control a noise level data storage to store noise level data in accordance with a frequency and a reception depth;
   compare the noise level data stored in the noise level data storage with data of the frequency spectrum, thereby to set a frequency band of the frequency spectrum for calculation; and
   calculate the frequency change rate in the frequency band.

3. The ultrasound diagnosis apparatus according to claim 2,
   wherein the processor is configured to:
   compare the data of the frequency spectrum with the noise level data, at a same frequency, thereby to extract a noise frequency band that is a band of a frequency corresponding to noise; and
   exclude the noise frequency band to set the frequency band.

4. The ultrasound diagnosis apparatus according to claim 3,
   wherein the processor is configured to extract, as the noise frequency band, a frequency band higher than a predetermined frequency.

5. The ultrasound diagnosis apparatus according to claim 3,
   wherein the processor is configured to extract, as the noise frequency band, a region in which a value of the data of the frequency spectrum is equal to or less than a threshold.

6. The ultrasound diagnosis apparatus according to claim 5,
   wherein the threshold is a value equal to or higher than the noise level data.

7. The ultrasound diagnosis apparatus according to claim 1,
   wherein the processor is configured to:
   calculate the second-order change rate for each of sound rays of the ultrasound;
   calculate an attenuation rate for each of the sound rays using the second-order change rate for each of the sound rays; and
   calculate statistics of the attenuation rate for each of all the sound rays in the scanning region to estimate the attenuation rate.

8. The ultrasound diagnosis apparatus according to claim 2,
   wherein the processor is configured to:
   perform, in the frequency band, regression analysis using a frequency as a variable, on a function defined by a difference between the frequency spectrum and the frequency spectrum at a reference reception depth, thereby to calculate a regression line;
   perform second regression analysis on a slope of the regression line using a reciprocating distance between the ultrasound transducer and the subject as a variable, thereby to calculate a second regression line; and
   determine a slope of the second regression line as the second-order change rate.

9. The ultrasound diagnosis apparatus according to claim 2,
   wherein the processor is configured to:
   perform regression analysis using a reciprocating distance between the ultrasound transducer and the subject as a variable, on the frequency spectrum in a distance section defined per frequency based on the frequency band, thereby to calculate a regression line;

perform second regression analysis on a slope of the regression line using the frequency as a variable, thereby to calculate a second regression line; and determine a slope of the second regression line as the second-order change rate.

10. The ultrasound diagnosis apparatus according to claim 1, wherein the processor is configured to:

generate B-mode image data as the ultrasound image displayed by converting amplitude of the ultrasound signal into brightness; and generate combined image data using information on the attenuation rate and using the B-mode image data.

11. The ultrasound diagnosis apparatus according to claim 1, wherein the processor is configured to:

calculate statistics of the attenuation rate for each of a plurality of partial regions obtained by dividing the scanning region to estimate the attenuation rate of each of the partial regions; and attach visual information in accordance with a value of the attenuation rate of each of the partial regions to generate attenuation rate map data.

12. The ultrasound diagnosis apparatus according to claim 11, wherein the processor is configured to:

generate B-mode image data as the ultrasound image displayed by converting amplitude of the ultrasound signal into brightness; and generate combined image data using the attenuation rate map data and using the B-mode image data.

13. The ultrasound diagnosis apparatus according to claim 2, wherein the processor is configured to control the noise level data storage to store the noise level data corresponding to the ultrasound transducer of the ultrasound probe that is connectable to the ultrasound diagnosis apparatus.

14. A method comprising:

analyzing, by a processor comprising hardware, a frequency of an ultrasound signal obtained by an ultrasound probe comprising an ultrasound transducer configured to transmit ultrasound to a subject and receive the ultrasound reflected from the subject, thereby calculating a frequency spectrum of the ultrasound signal for each reception depth;

calculating, by the processor, in a predetermined order, a distance change rate and a frequency change rate in the frequency spectrum or in a function defined by using the frequency spectrum, thereby calculating a second-order change rate of the frequency spectrum or of the function;

estimating, by the processor, an attenuation rate of the ultrasound signal, per unit distance and per unit frequency, in a predetermined region within a scanning region of the ultrasound transducer using the second-order change rate, wherein the attenuation rate is estimated based on an equation:

$$\partial^2 \psi(f,L)/\partial L \partial f = -\zeta$$

where $\zeta$ is the attenuation rate, by using a function:

$$\psi(f,L) = F(f,L) - F(f,0)$$

wherein the right side of the equation can be replaced with $\partial^2 \psi(f, L)/\partial f \partial L$ obtained by a procedure comprising:

(i) in a possible range of a reciprocating distance (L), a slope (the frequency change rate) of a regression line of the frequency f of the function $\psi(f, L)$, the slope being an approximate value of $\partial \psi(f, L)/\partial f$;

(ii) a slope (the distance change rate) of a regression line for the reciprocating distance L of the approximate values of $\partial \psi(f, L)/\partial f$ is obtained, the slope being an approximate value of $\partial^2 \psi(f, L)/\partial f \partial L$; and (iii) the approximate value of $\partial^2 \psi(f, L)/\partial f \partial L$ is multiplied by −1 to obtain an approximate value of the attenuation rate $\zeta$ as represented by the equation; and generating, by the processor, an ultrasound image based on the ultrasound signal, and performing, by the processor, image processing on the ultrasound image based on the attenuation rate.

15. A non-transitory computer-readable recording medium with an executable program stored thereon, the program causing a computer to execute:

analyzing a frequency of an ultrasound signal obtained by an ultrasound probe comprising an ultrasound transducer configured to transmit ultrasound to a subject and receive the ultrasound reflected from the subject, thereby calculating a frequency spectrum of the ultrasound signal for each reception depth;

calculating, in a predetermined order, a distance change rate and a frequency change rate in the frequency spectrum or in a function defined by using the frequency spectrum, thereby calculating a second-order change rate of the frequency spectrum or of the function;

estimating an attenuation rate of the ultrasound signal, per unit distance and per unit frequency, in a predetermined region within a scanning region of the ultrasound transducer using the second-order change rate, wherein the attenuation rate is estimated based on an equation:

$$\partial^2 \psi(f,L)/\partial L \partial f = -\zeta$$

where $\zeta$ is the attenuation rate, by using a function:

$$\psi(f,L) = F(f,L) - F(f,0)$$

wherein the right side of the equation can be replaced with $\partial^2 \psi(f, L)/\partial f \partial L$ obtained by a procedure comprising:

(i) in a possible range of a reciprocating distance (L), a slope (the frequency change rate) of a regression line of the frequency f of the function $\psi(f, L)$, the slope being an approximate value of $\partial \psi(f, L)/\partial f$;

(ii) a slope (the distance change rate) of a regression line for the reciprocating distance L of the approximate values of $\partial \psi(f, L)/\partial f$ is obtained, the slope being an approximate value of $\partial^2 \psi(f, L)/\partial f \partial L$; and (iii) the approximate value of $\partial^2 \psi(f, L)/\partial f \partial L$ is multiplied by −1 to obtain an approximate value of the attenuation rate $\zeta$ as represented by the equation; and generating an ultrasound image based on the ultrasound signal and performing image processing on the ultrasound image based on the attenuation rate.

16. An ultrasound diagnosis apparatus comprising:
a processor comprising hardware, wherein the processor is configured to:
analyze a frequency of an ultrasound signal obtained by an ultrasound probe comprising an ultrasound transducer configured to transmit ultrasound to a subject and receive the ultrasound reflected from the subject, thereby to calculate a frequency spectrum of the ultrasound signal for each reception depth;
calculate, in a predetermined order, a distance change rate and a frequency change rate in the frequency spectrum or in a function defined by using the frequency spectrum, thereby to calculate a second-order change rate of the frequency spectrum or of the function;
estimate an attenuation rate of the ultrasound signal, per unit distance and per unit frequency, in a predetermined region within a scanning region of the ultrasound transducer using the second-order change rate; and
generate an ultrasound image based on the ultrasound signal, and perform image processing on the ultrasound image based on the attenuation rate,
wherein the attenuation rate is estimated based on an equation:

$$\partial 2\psi(f,L)/\partial f\partial L = -\zeta$$

where $\zeta$ is the attenuation rate,
by using a function:

$$\psi(f,L) = F(f,L) - F(f,0)$$

wherein the right side of the equation can be replaced with $\partial 2\psi(f, L)/\partial f\partial L$ obtained by a procedure comprising:
(i) in a possible range of a frequency f, a slope (the distance change rate) of a regression line of a reciprocating distance L of an approximate value of the function $\psi(f, L)$ is obtained, the slope being an approximate value of act $\partial\psi(f, L)/\partial L$;
(ii) a slope (the frequency change rate) of a regression line for the frequency f of the approximate values of $\partial\psi(f, L)/\partial L$ is obtained, the slope being an approximate value of $\partial 2\psi(f, L)/\partial f\partial L$; and
(iii) the approximate value of $\partial 2\psi(f, L)/\partial f\partial L$ is multiplied by −1 to obtain an approximate value of the attenuation rate $\zeta$ as represented by the equation.

* * * * *